(12) United States Patent
McKernan

(10) Patent No.: US 10,358,673 B2
(45) Date of Patent: *Jul. 23, 2019

(54) METHOD OF AMPLIFYING NUCLEIC ACID SEQUENCES

(71) Applicant: Courtagen Life Sciences, Inc., Woburn, MA (US)

(72) Inventor: Kevin J. McKernan, Marblehead, MA (US)

(73) Assignee: Courtagen Life Sciences, Inc., Woburn, MA (US)

(*) Notice: Subject to any disclaimer, the term of this patent is extended or adjusted under 35 U.S.C. 154(b) by 415 days.

This patent is subject to a terminal disclaimer.

(21) Appl. No.: 15/358,841

(22) Filed: Nov. 22, 2016

(65) Prior Publication Data
US 2017/0073732 A1    Mar. 16, 2017

Related U.S. Application Data

(63) Continuation of application No. 15/099,230, filed on Apr. 14, 2016, now Pat. No. 9,512,472, which is a continuation of application No. 14/341,540, filed on Jul. 25, 2014, now Pat. No. 9,422,594, which is a continuation of application No. PCT/US2013/063931, filed on Oct. 8, 2013.
(Continued)

(51) Int. Cl.
| | |
|---|---|
| C12Q 1/68 | (2018.01) |
| C12Q 1/6806 | (2018.01) |
| C12Q 1/6848 | (2018.01) |
| C12Q 1/686 | (2018.01) |

(52) U.S. Cl.
CPC ........... *C12Q 1/6806* (2013.01); *C12Q 1/686* (2013.01); *C12Q 1/6848* (2013.01)

(58) Field of Classification Search
None
See application file for complete search history.

(56) References Cited

U.S. PATENT DOCUMENTS

| | | | |
|---|---|---|---|
| 5,536,649 A | 6/1996 | Fraiser et al. | |
| 7,687,247 B1 * | 3/2010 | Hartley | C12Q 1/6848 435/6.12 |

(Continued)

FOREIGN PATENT DOCUMENTS

| | | |
|---|---|---|
| EP | 2 330 214 A1 | 9/2005 |
| WO | WO 2006/009870 A2 | 1/2006 |

(Continued)

OTHER PUBLICATIONS

Oyola et al. (Efficient Depletion of Host DNA Contamination in Malaria Clinical Sequencing, J Clin Microbiol. Mar. 2013;51(3):745-51. doi: 10.1128/JCM.02507-12. Epub Dec. 5, 2012).*
(Continued)

*Primary Examiner* — Aaron A Priest
(74) *Attorney, Agent, or Firm* — Hamilton, Brook, Smith & Reynolds, P.C.

(57) ABSTRACT

The invention is directed to methods of removing amplicons of non target and/or target nucleic acid sequences having one or more modified (e.g., methylated) nucleotides from a sample wherein the sample comprises the non target nucleic acid and a target nucleic acid sequence to be amplified.

14 Claims, 23 Drawing Sheets

Specification includes a Sequence Listing.

Related U.S. Application Data

(60) Provisional application No. 61/729,072, filed on Nov. 21, 2012.

(56) References Cited

U.S. PATENT DOCUMENTS

| | | | |
|---|---|---|---|
| 9,512,472 B2 | 12/2016 | McKernan | |
| 2003/0228620 A1 | 12/2003 | Du Breuil Lastrucci | |
| 2005/0202490 A1 | 9/2005 | Makarov et al. | |
| 2008/0311627 A1* | 12/2008 | Tetzner | C12Q 1/6848 435/91.2 |
| 2010/0167942 A1 | 7/2010 | Zheng et al. | |
| 2011/0207139 A1 | 8/2011 | Lubys et al. | |
| 2013/0337460 A1 | 12/2013 | Forsyth | |
| 2014/0178873 A1* | 6/2014 | Brachmann | C12Q 1/6858 435/6.11 |
| 2014/0335569 A1 | 11/2014 | McKernan | |

FOREIGN PATENT DOCUMENTS

| | | |
|---|---|---|
| WO | WO 2012/055408 A1 | 5/2012 |
| WO | WO 2012/055409 A1 | 5/2012 |
| WO | WO 2013/003376 A2 | 1/2013 |

OTHER PUBLICATIONS

Aird, D., et al., "Analyzing and Minimizing PCR Amplification Bias in Illumina Sequencing Libraries", *Genome Biology*, 12:R18, 14 pages (2011).
Bensasson, D., et al., "Mitochondrial Pseudogenes: Evolution's Misplaced Witnesses", *Trends in Exology & Evolution*, 16(6): 314-321 (2001).
Bormann, C.A., et al., "Whole Methylome Analysis by Ultra-Deep Sequencing Using Two-Base Encoding", *PLoS One*, 5(2): e9320, 8 pages (2010).
Burman, R.W., et al., "Hypomethylation of an Expanded FMR1 Allele Is Not Associated With a Global DNA Methylation Defect", *Am J Hum Genet.*, 65: 1375-1386 (1999).
Cantara, W.A., et al., "Expanded Use of Sense Codons Is Regulated by Modified Cytidines in tRNA", *PNAS*, 110(27): 6 pages (2013).
Champlot, S., et al., "An Efficient Multistrategy DNA Decontamination Procedure of PCR Reagents for Hypersensitive PCR Applications", *PLoS One*, 5(9): e 13042, 15 pages (2010).
Chiu, R.W.K, et al., "Maternal Plasma DNA Analysis With Massively Parallel Sequencing by Ligation for Noninvasive Prenatal Diagnosis of Trisomy 21", *Clinical Chemistry*, 56(3): 459-463 (2010).
Chotai, K.A. and Payne, S.J., "A Rapid, PCR Based Test for Differential Molecular Diagnosis of Prader-Willi and Angelman Syndromes", *J Med Genet*, 35: 472-475 (1998).
Clark, T. A., et al., "Characterization of DNA Methyltransferase Specificities Using Single-Molecule, Real-Time DNA Sequencing", *Nucleic Acids Research*, 40(4): e29, 12 pages (2012).
Cohen-Karni, D., et al., "The MspJI Family of Modification—Dependent Restriction Endonucleases for Epigenetic Studies", *PNAS*, 108(27): 11040-11045 (2011).
Cokus, S.J., et al., "Shotgun Bisulphite Sequening of the *Arabidopsis* Genome Reveals DNA Methylation Patterning", *Nature*, 452:215-219 with 54 pages of supplementary information (2008).
Cui, H., et al., "Comprehensive Next-Generation Sequence Analysses of the Entire Mitochondrial Genome Reveal New Insights Into the Molecular Diagnosis of Mitochondrial DNA Disorders", *Genetics in Medicine*, 15(5): 388-394 (2013).
Anonymous; "Dam-Dcm and CpG Methylation"[online], 2016 [retrieved on Aug. 25, 2016], XP055297583; retrieved from the Internet URL: https://www.ned.com/tools-and-resources/selection-charts/dam-dcm-and-cpg-methylation?device=pdf.
Damas, J., et al., "Mitochondrial DNA Deletions Are Associated With Non-B DNA Conformations", *Nucleic Acids Research*, 40(16): 7606-7621 (2012).

Epicentre, Nextra™ DNASample Prep Kit, URL: http://www.epibio.com/docs/defaultsource/protocols/nextra-dna-sample-prep-kit-(roche-fix-compatible).pdf?sfvrsn=6, 9 pages, Dec. 17, 2009.
Falk, M.J., et al., "Mitochondrial Disease Genetic Diagnostics: Optimized Whole Exome Analysis for All MitoCarta Nuclear Genes and the Mitochondrial Genome", *Discov Med*, 14(79): 389-399 (2012).
Fang, G., et al., "Genome-Wide Mapping of Methylated Adenine Residues in Pathogenic *Escherichia coli*, Using Single-Molecule Real-Time Sequencing", *Nature Biotechnology*, 30(12): 1232-1239 (2012).
Flusberg, B.A., et al., "Direct Detection of DNA Methylation During Single-Molecule Real-Time Sequencing", *Nature Methods*, 7(6): 461-465 (2010).
Frackman, S., et al., "Betaine and DMSO: Enhancing Agents for PCR", *Promega Notes*, 65: 27-30 (1998).
Gargis, A.S., et al., "Assuring the Quality of Next-Generation Sequencing in Clinical Laboratory Practice", *Nature Biotechnology*, 30(11): doi: 10.1038/nbt2403, 5 pages (2012).
Gilissen, C., et al., "Exome Sequencing Identifies WDR35 Variants Involved in Sensenbrenner Syndrome", *The American Journal of Human Genetics*, 87: 418-423 (2010).
Gilissen, C., et al., "Unlocking Mendelian Disease Using Exome Sequencing", *Genome Biology*, 12(228): 11 pages (2011).
Gilissen, C., et al., "Disease Gene Identification Stategies for Exome Sequencing", *European Journal of Human Genetics*, 20: 490-497 (2012).
Gowher, H., et al., "DNA of *Drosphila melanogaster* Contains 5-Methylcytosine", *The EMBO Journal*, 19(24): 6918-6923 (2000).
Haack, T.B., et al., "Exome Sequencing Identifies ACAD9 Mutations As a Cause of Complex I Deficiency", *Nature Genetics*, 42(12): 1131-1134 (2010).
Hartley, J.L. and Rashtchian, A., "Dealing With Contamination: Enzymatic Control of Carryover Contamination in PCR", PCR Methods and Applications, Cold Spring Harbor Laboratory, 3:S10-S14 (1993).
Hazkani-Covo, E., et al., "Molecular Poltergeists: Mitochondrial DNA Copies (numts) in Sequenced Nuclear Genomes", *PLoS Genetics*, 6(2): e100834, 11 pages (2010).
Heyn, H., et al., "DNA Methylation Contributes to Natural Human Variation", *Genome Research*, 23:1363-1372 (2013).
Holliday, R. and Ho, T., "Gene Silencing in Mammalian Cells by Uptake of 5-Methyl Deoxycytidine-5'-Triphosphate", *Somatic Cell and Molecular Genetics*, 17(6): 537-542 (1991).
Holliday, R. and Ho., T., "Evidence for Gene Silencing by DNA Methylation in Normal Human Diploid Fibroblasts", *Somatic Cell and Molecular Genetics*, 21(3): 215-218 (1995).
Holliday, R. and Ho. T., "Evidence for Gene Silencing by Endogenous DNA Methylation", *Proc. Natl. Acad. Sci.*, 95: 8727-8732 (1998).
Homer, N., et al., "Resolving Individals Contributing Trace Amounts of DNA to Highly Complex Mixtures Using High-Density SNP Genotyping Microarrays", *PLoS Genetics*, 4(8): e1000167, 9 pages (2008).
Hong, E.E., et al., Regionally-Specific and Gnome-Wide Analyses conclusively Demonstrate the Absence of CpG Methylation in Human Mitochondrial DNA, *Mol. Cell. Biol.*, 33: 27 pages (2013).
Horton, J.R., et al., "Structure and Cleavage Activity of the Tetrameric MspJI DNA Modification—Dependent Restriction Endonuclease", *Nucleic Acids Research*, 40(19): 9763-9773 (2012).
Hublarova, P., et al., "Prediction of Human Papillomavirus 16 E6 Gene Expression and Cervical Intraepithelial Neoplasia Progression by Methylation Status", *International Journal of Gynecological Cancer*, 19(3): 321-325 (2009).
Huh, Y.H., et al., "Higher 5-Hydroxymethylcytosine Identifies Immortal DNA Strand Chromosomes in Asymmetrically Self-Renewing Disturbed Stem Cells", *PNAS*, 110(42):16862-16867 (2013).
Igartua, C., et al., "Targeted Enrichment of Specific Regions in the Human Genome by Array Hybridization", *Curr Protoc Hum Genet*, Chapter Unit 18.3, 22 pages (2010).
Irizarry, R.A., et al., "Comprehensive High-Throughput Arrays for Relative Methylation (CHARM)", Genome Research, 18: 780-790 (2008).

(56) References Cited

OTHER PUBLICATIONS

Jin, S.G., et al., "Genomic Mapping of 5-Hydroxymethylcytosine in the Human Brain", *Nucleic Acids Research*, 39(12): 5015-5024 (2011).

Johansson, H., et al., "Targeted Resequencing of Candidate Genes Using Selector Probes", *Nucleic Acids Research*, 39(2): e8, 13 pages (2010).

Keith, J.M., et al., "Algorithms for Sequence Analysis Via Mutagenesis", *Bioinformatics*, 20(152004): 2401-2410 (2004).

Keith, J.M., et al., "Unlocking Hidden Genomic Sequence", *Nucleic Acids Research*, 32(3): e35, 9 pages (2004).

Keller, I., et al., "Transition—Transversion Bias Is Not Universal: A Counter Example From Grasshopper Pseudogenes", *PLoS Genetics*, 3(2): e22, 0185-0191 (2007).

Kinney, S.M., et al., "Tissue-Specific Distribution and Dynamic Changes of 5-Hydroxymethylcytosine in Mammalian Genomes", *The Journal of Biological Chemistry*, 286(28):24685-24693 (2011).

Klassen, T., et al., "Exome Sequencing of Ion Channel Genes Reveals Complex Variant Profiles Confounding Personal Risk Assessment in Epilepsy", *Cell*, 145(7): 1036-1048 (2011).

Korlach, J. and Turner, S.W., "Going Beyond Five Bases in DNA Sequencing", *Current Opinion in Structural Biology*, 22:251-261 (2012).

Kozarewa, I., et al., "Amplification-Free Illumina Sequencing-Library Preparation Facilitates Improved Mapping and Assembly of GC-Biased Genomes", *Nat Methods*, 6(4): 291-295 (2009).

Kraus, T.F.J., et al., "Low Values of 5-Hydroxymethylcytosine (5hmC), The 'Sixth Base,' Are Associated With Anaplasia in Human Brain Tumors", *International Journal of Cancer*, 131: 1577-1590 (2012).

Kreuder, J., et al., "Rapid Detection of Mitochondrial Deletions by Long-Distance Polymerase Chain Reaction", *European Journal of Pediatrics*, 154: 996 (1995).

Kriaucionis, S. and Heintz, N., "The Nuclear DNA Base, 5-Hydroxymethlcytosine Is Present in Brain and Enriched in Purkinje Neurons", *Science*, 324(5929): 929-930 (2009).

Kuwahara, M., et al., "Simultaneous Incorporation of Three Different Modified Nucleotides During PCR", *Nucleic Acids Research Supplement*, 3: 37-38 (2003).

Lalueza-Fox, C. and Gilbert, M.T.P., "Paleogenomics of Archaic Hominins", *Current Biology*, 21: F1002-R1009 (2011).

Langmead, B., et al., "Ultrafast and Memory-Efficient Alignment of Short DNA Sequences to the Human Genome", *Genome Biology*, 10: R25, 10 pages (2009).

Lay, M.J. and Wittwer, C.T., "Real-Time Fluorescence Genotyping of Factor V Leiden During Rapid-Cycle PCR", *Clinical Chemistry*, 43(12): 2262-2267 (1997).

Levene, M.J., et al., "Zero-Mode Waveguides for Single Molecule Analysis At High Concentrations", *Science*, 299: 682-686 (2003).

Li, J., et al., "Replacing PCR With COLD-PCR Enriches Variant DNA Sequences and Redefines the Sensitivity of Genetic Testing", *Nature Medicine*, 14(5): 579-584 (2008).

Li, M., et al., "Fidelity of Capture-Enrichment for mtDNA Genome Sequencing: Influence of NUMTs", *Nucleic Acids Research*, 40(18): e137, 8 pages (2012).

Li, T.W. and Weeks, K.M., "Structure-Independent and Quantitative Ligation of Single-Stranded DNA", *Analytical Biochemistry*, 349: 242-246 (2006).

Lister, R. and Ecker, J.R., "Finding the Fifth Base: Genome-Wide Sequencing of Cytosine Methylation", *Genome Research*, 19:959-966 (2009).

Longo, M.C., et al., "Use of Uracil DNA Glycosylase to Control Carry-Over Contamination in Polymerase Chain Reactions", *Gene*, 93: 125-128 (1990).

Lopez, J.V., et al., "Numt, A Recent Transfer and Tandem Amplification of Mitochondrial DNA to the Nuclear Genome of the Domestic Cat", *J Mol Evol*, 39: 174-190 (1994).

Lyko, F., et al., "Mammalian (Cytosine-5) Methyltransferases Cause Genomic DNA Methylation and Lethality in *Drosophila*", *Nature Genetics*, 23: 363-366 (1999).

McKenna, A., et al., "The Genome Analysis Toolkit: A MapReduce Framework for Analyzing Next-Generation DNA Sequencing Data", *Genome Research*, 20: 1297-1303 (2010).

McKernan, K.J., et al., "DREAMing of a Patent-Free Human Genome for Clinical Sequencing", *Nature Biotechnology*, 31(10): 884-887 (2013).

McMurray, A.A., et al., "Short-Insert Libraries As a Method of Problem Solving in Genome Sequencing", *Genome Research*, 8: 562-566 (1998).

Mita, S., et al., "Recombination Via Flanking Direct Repeats Is a Major Cause of Large-Scale Deletions of Human Mitochondrial DNA", *Nucleic Acids Res.*, 18(3): 561-567 (1990).

Münzel, M., et al., "Quantification of the Six DNA Base Hydroxymethylcytosine in the Brain", *Agnew. Chem, Int. Ed.*, 49: 5375-5377 (2010).

Münzel, M., et al., "5-Hydroxymethylcytosine, The Sixth Base of the Genome", *Agnew. Chem. Int. Ed.*, 50:6460-6468 (2011).

Murray, I.A., et al., "The Methylomes of Six Bacteria", *Nucleic Acids Research*, 40(22): 11450-11462 (2012).

Nestor C., et al., "Enzymatic Approaches and Bisulfite Sequencing Cannot Distinguish Between 5-Methylcytosine and 5-Hydroxymethylcytosine in DNA", *BioTechniques*, 48(4): 317-319 (2010).

New England Biolabs, Inc. Epigenetics, Understanding Histone & DNA Modification, 49 pages (2011).

New England Bioloabs, McrBC product information; 4 pages, URL: https://www.neb.com/products/M0272-McrBC, downloaded Jul. 24, 2014.

Ng, S.B., et al., "Targeted Capture and Massively Parallel Sequencing of Twelve Human Exomes", *Nature*, 461(7261): 272-276 (2009).

Oyola, S. O., et al., "Efficient Depletion of Host DNA Contamination in Malaria Clinical Sequencing", *Journal of Clinical Microbiology*, 51(3):745-751 (2013).

Pak, J. and Fire, A., "Distinct Populations of Primary and Secondary Effectors During RNAi in *C. elegans*" *Science*, 315: 241-244 (2007).

Panne, D., et al., "The McrBC Endonuclease Translocates DNA in a Reaction Dependent on GTP Hydrolysis", *J. Mol. Biol.*, 290: 49-60 (1999).

Peak, M.J., et al., "Extreme Resistance to Thermally Induced DNA Backbone Breaks in the Hyperthermophilic Archaeon *Pyrococcus furiosus*", *Journal of Bacteriology*, 177(21): 6316-6318 (1995).

Peters, B.A., et al., "Accurate Whole-Genome Sequencing and Haplotyping From 10 to 20 Human Cells", *Nature*, 487: 190-194 (2012).

Quinlan, A.R. and Hall, I.M., "BEDTools: A Flexible Suite of Utilities for Comparing Genomic Features", *Bioinformatics*, 26(6): 841-842 (2010).

Raleigh, E.A., "Organization and Function of the mcrBC Genes of *Escherichia coli* K-12", *Molecular Microbiology*, 6(9): 1079-1086 (1992).

Ratel, D., et al., "N6-Methyladenine: The Other Methylated Base of DNA", *BioEssays*l, 28:309-315 (2006).

Ricchetti, M., et al., "Continued Colonization of the Human Genome by Mitochondrial DNA", *PLoS Biology*, 2(9): e273, 1313-1324 (2004).

Richly, E. and Leister, D., "NUMTs In Sequenced Eukaryotic Genomes", *Molecular Biology and Evolution*, 21(6): 1081-1084 (2004).

Ririe. K.M., et al., "Product Differentiation by Analysis of DNA Melting Curves During the Polymerase Chain Reaction", *Analytical Biochemistry*, 245: 154-160 (1997).

Santoso, B., et al., "Control of Organ-Specific Demethylation by an Element of the T-Cell Receptor-α Locus Control Region", *The Journal of Biological Chemistry*, 275(3): 1952-1958 (2000).

Sato, N., et al. "Genome-Wide DNA Methylation Analysis Reveals Phytoestrogen Modification of Promoter Methylation Patterns During Embryonic Stem Cell Differentiation", *PLoS One*, 6(4):e19278, 13 pages (2011).

Schiffman, J.D., et al., "Molecular Inversion Probes Reveal Patterns of 9p21 Deletion and Copy Number Aberrations in Childhood Leukemia", *Cancer Genet Cytogenet*, 193: 9-18 (2009).

(56) References Cited

OTHER PUBLICATIONS

Song, C.X., et al., "Sensitive and Specific Single-Molecule Sequencing of F-Hydroxymethylcytosine", *Nature Methods*, 9: 75-77 (2013).
Stewart, F.J., et al., "Dependence of McrBC Cleavage on Distance Between Recognition Elements", *Biol. Chem.*, 379: 611-616 (1998).
Stewart, F.J., et al., "Methyl-Specific DNA Binding by McrBC, A Modification-Dependent Restriction Enzyme", *J. Mol. Biol.*, 298: 611-622 (2000).
Sun, Z., et al., "High-Resolution Enzymatic Mapping of GEnomic 5-Hydroxymethylcytosine in Mouse Embryonic Stem Cells", *Cell Resp*, 3(2): 567-576 (2013).
Sutherland, E., et al., "McrBC: A Multisubunit GTP-Dependent Restriction Endonuclease", *J. Mol. Biol.*, 225: 327-348 (1992).
Szwagierczak, A., et al., "Characterization of PvuRtsII Endonuclease As a Tool to Investigate Genomic 5-Hydroxymethylcytosine", *Nucleic Acids Research*, 39(12): 5149-5156 (2011).
Tahiliani, M., et al., "Conversion of 5-Methylcytosine to 5-Hydroxymethylcytosine in Mammalian DNA by MLL Partner TET1", *Science*, 324(5929): 930-935 (2009).
Tarnopolsky, M., et al., "Severe Infantile Leigh Syndrome Associated With a Rare Mitochondrial ND6 Mutations, m.14487T.C", *American Journal of Medical Genetics*, Part A, 161A: 2020-2023 (2013).
Trakadis, Y.J., "Patient-Controlled Encrypted Genomic Data: An Approach to Advance Clinical Genomics", *BMC Medical Genomics*, 5(31): 11 pages (2012).
Valouev, A., et al., "A High-Resolution, Nucleosome Position Map of *C. elegans* Reveals a Lack of Universal Sequence-Dictated Positioning", *Genome Research*, 18: 1051-1063 (2008).
Von Ashen, N., et al., "Oligonucleotide Melting Temperatures Under PCR Conditions: Nearest-Neighbor Corrections for $Mg^{2+}$, Deoxynucleotide Triphosphate, and Dimethyl Sulfoxide Concentrations With Comparison to Alternative Empirical Formulas", *Clinical Chemistry*, 47(11): 1956-1961 (2001).
Wagner, I. and Capesious, I., "Determination of 5-Methylcytosine From Plant DNA by High-Performance Liquid Chromatography", *Biochimica et Biophysica Acta*, 654: 52-56 (1981).
Wang, H., et al., "Comparative Characterization of the PvuRtsII Family of Restriction Enzymes and Their Application in Mapping Genomic 5-Hydroxymethylcytosine", *Nucleic Acids Research*, 39(21): 9294-9305 (2011).
Wanunu, M., et al., "Discrimination of Methylcytosine From Hydroxymethylcytosine in DNA Molecules", *J. Am. Chem. Soc.*, 133: 486-492 (2011).
Wardle, J., et al., "Uracil Recognition by Replicative DNA Polymerases Is Limited to the Archaea, Not Occurring With Bacteria and Eukarya", *Nucleic Acids Research*, 36(3): 705-711 (2008).
Wong, K.K. and McClelland, M., "PCR With 5-Methyl-dCTP Replacing dCTP", *Nucleic Acids Research*, 19(5): 1081-1085 (1991).
Wong, K.K., et al., "A Novel Method for Producing Partial Restriction Digestion of DNA Fragments by PCR with 5-Methyl-CTP", *Nucleic Acids Research*, 25(20):4169-4171 (1997).
Xu, Y. and Kool, E.T., "A Novel 5'-Iodonucleoside Allows Efficient Nonenzymatic Ligation of Single-Stranded and Duplex DNAs", *Tetrahedron Lett.*, 38(32): 5595-5598 (1997).
Zhelkovsky, A.M. and McReynolds, L.A., "Simple and Efficient Synthesis of 5' Pre-Adenylated DNA Using Thermostable RNA Ligase", *Nucleic Acids Research*, 39(17): e117, 6 pages (2011).
Zheng, Yu, et al., "A Unique Family of Mrr-Like Modification-Dependent Restriction Endonucleases", *Nucleic Acids Research*, 38(16): 5527-5534 (2010).
Zhou, Y., et al., "Undermethylated DNA as a Source of Microsatellites From a Conifer Genome", *Genome*, 45: 91-99 (2002).
Notification of Transmittal of the International Search Report for and the Written Opinion of the International Searching Authority for PCT/US2013/063931, "Method of Amplifying Nucleic Acid Sequences", dated Apr. 23, 2014.
Notification Concerning Transmittal of Intenational Report on Patentability for PCT/US2013063931, "Method of Amplifying Nucleic Acid Sequences", dated Jun. 4, 2015.
Non-final Office Action for U.S. Appl. No. 14/341,540, "Method of Amplifying Nucleic Acid Sequences", dated Oct. 7, 2014.
Final Office Action for U.S. Appl. No. 14/341,540, "Method of Amplifying Nucleic Acid Sequences", dated Dec. 24, 2014.
Non-final Office Action for U.S. Appl. No. 14/341,540, "Method of Amplifying Nucleic Acid Sequences", dated Jul. 20, 2015.
Notice of Allowance for U.S. Appl. No. 14/341,540, "Method of Amplifying Nucleic Acid Sequences", dated Feb. 18, 2016.
Notice of Allowability for U.S. Appl. No. 14/341,540, "Method of Amplifying Nucleic Acid Sequences", dated Mar. 4, 2016.
Notice of Allowance for U.S. Appl. No. 15/099,230, "Method of Amplifying Nucleic Acid Sequences", dated Aug. 26, 2016.

* cited by examiner

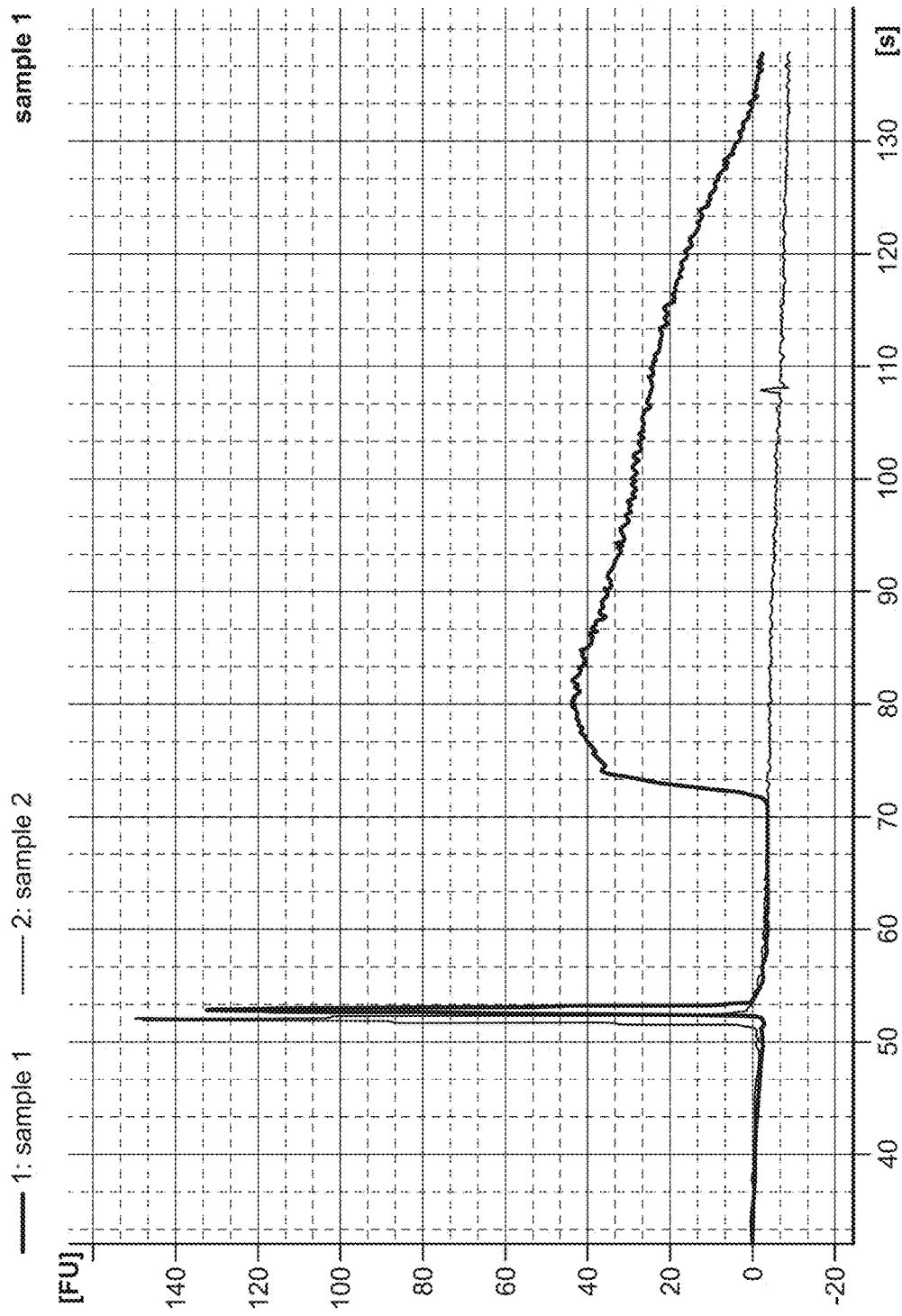

METHOD OF AMPLIFYING NUCLEIC ACID SEQUENCES

RELATED APPLICATIONS

This application is a continuation of U.S. application Ser. No. 15/099,230, filed Apr. 14, 2016, which is a continuation of U.S. application Ser. No. 14/341,540, filed Jul. 25, 2014, now U.S. Pat. No. 9,422,594, which is a continuation of International Application No. PCT/US2013/063931, which designated the United States and was filed on Oct. 8, 2013, published in English and claims the benefit of U.S. Provisional Application No. 61/729,072, filed on Nov. 21, 2012. The entire teachings of the above applications are incorporated herein by reference.

INCORPORATION BY REFERENCE OF MATERIAL IN ASCII TEXT FILE

This application incorporates by reference the Sequence Listing contained in the following ASCII text file being submitted concurrently herewith:
a) File name: 47231011006SEQUENCELISTING.txt; created Nov. 22, 2016, 3 KB in size.

BACKGROUND OF THE INVENTION

Many clinical labs rely on uracil DNA glycosylase (UDG) (also known as uracil N-glycosylase (UNG)) decontamination of polymerase chain reaction (PCR) products. Amplicons containing uracil as opposed to thymidine can be digested with UDG to eliminate any residual PCR product in the laboratory. Many Next Generation sequencing platforms utilize polymerases that cannot traverse a uracil (utilize polymerases that are uracil illiterate). For instance, the Illumina MiSeq and HiSeq platforms rely on polymerases with proof reading activity to generate the seeded clusters for surface PCR. Proof reading polymerases such as pfu will stall on uracils in the template strand. Due to this, amplification of uracilyated templates fail to initiate cluster PCR thus eliminating the potential of UDG decontamination methods.

Thus, improved amplification methods and/or decontamination of amplification methods are needed for nucleic acid amplification techniques such as PCR.

SUMMARY OF THE INVENTION

In some aspects, the invention is directed to a method of removing amplicons of non target nucleic acid sequence having one or more modified (e.g., methylated) nucleotides from a sample wherein the sample comprises the non target nucleic acid sequence and a target nucleic acid sequence to be amplified. The method comprises contacting the sample with a composition comprising a restriction enzyme that cleaves (e.g., specifically (selectively) cleaves (recognizes)) a nucleic acid sequence comprising the modified nucleotides (e.g., a methyl specific restriction enzyme) and that is capable of being deactivated, thereby producing a combination; maintaining the combination under conditions in which the amplicons of the non target nucleic acid are digested by the restriction enzyme (e.g., methyl specific restriction enzyme) prior to amplification of the target nucleic acid; and amplifying the target nucleic acid sequence thereby producing amplicons of the target nucleic acid sequence, and thereby removing the amplicons of the non target nucleic acid from the sample comprising the target nucleic acid sequence to be amplified.

In other aspects, the invention is directed to a method of serially amplifying a target nucleic acid sequence wherein the first amplification is performed with a first cleavable base and a subsequent amplification is performed with a second cleavable base, and the first cleavable base and the second cleavable base are different. In some aspects, the first cleavable base is cleaved by a first restriction enzyme and the second cleavable base is a uniquely cleavable base that is cleaved by a second restriction enzyme that specifically cleaves amplicons comprising the uniquely cleavable base; the subsequent amplification is performed with the uniquely cleavable base and the second restriction enzyme; and the first amplification is performed with the first cleavable base wherein amplicons comprising the first cleavable base can be simultaneously cleaved with the first restriction enzyme that cleaves the different cleavable base.

In other aspects, the invention is directed to a method of removing amplicons of non target nucleic acid sequence having one or more nucleotides that are modified (e.g., methylated) from a sample wherein the sample comprises the non target nucleic acid sequence and a target nucleic acid sequence to be serially amplified. The method comprises contacting the sample with a composition (a first composition) comprising (i) deoxynucleotide triphophates (dNTPs) comprising dATP, dTTP, dGTP, and dCTP wherein one or more of the deoxynucleotide triphophates are modified (e.g., modified with a first moiety, e.g., methylated with a first methyl group) (ii) a nucleic acid polymerase, (iii) one or more primers that are complementary to a portion of the target nucleic acid sequence, and (iv) a first restriction enzyme (e.g., a (first) methyl specific restriction enzyme) that is capable of being deactivated and that digests nucleic acid sequences comprising nucleotides modified with the first moiety (e.g., that are methylated with the first methyl group), thereby producing a combination (a first combination). The combination is maintained under conditions in which the amplicons of the non target nucleic acid are digested by the first restriction enzyme (e.g., a methyl specific restriction enzyme) prior to amplification of the target nucleic acid. The target nucleic acid sequence is amplified, thereby producing amplicons of the target nucleic acid sequence having one or more modified nucleotides comprising the first moiety (e.g., nucleotides that are methylated with the first methyl group). The amplicons of the target nucleic acid sequence are contacted with a composition (second composition) comprising (i) deoxynucleotide triphosphates (dNTPs) comprising dATP, dTTP, dGTP, and dCTP wherein one or more of the deoxynucleotide triphosphates are modified (e.g., modified with a second moiety, e.g., methylated with a second methyl group), (ii) a nucleic acid polymerase, (iii) one or more primers that are complementary to a portion of the target nucleic acid sequence, and (iv) a second restriction enzyme (e.g., a (second) methyl specific restriction enzyme) that is capable of being deactivated and that selectively digests nucleic acid sequences comprising nucleotides modified with the second moiety (e.g., that are methylated with the second methyl group), thereby producing a combination (a second combination). The combination is maintained under conditions in which the amplicons of the non target nucleic acid are digested by the second restriction enzyme (e.g., the second methyl specific restriction enzyme) prior to amplification of the target nucleic acid. The target nucleic acid sequence is amplified, thereby producing amplicons of the target nucleic acid sequence having one or more nucleotides modified with the first moiety and the second moiety (amplicons of the target nucleic acid sequence that are methylated with the first methyl group and the second methyl group), thereby removing amplicons of the non target nucleic acid having one or more nucleotides that are modified (e.g., methylated) from a sample wherein the sample comprises the non target nucleic acid and a target nucleic acid sequence to be serially amplified.

In other aspects, the invention is directed to a method of removing amplicons of a target nucleic acid sequence after amplification of the target nucleic acid sequence. The method comprises contacting the target nucleic acid sequence with (i) deoxynucleotide triphophates (dNTPs) comprising dATP, dTTP, dGTP, and dCTP wherein one or more of the deoxynucleotide triphophates are modified (e.g., methylated) (ii) a nucleic acid polymerase, and (iii) one or more primers that are complementary to a portion of the target nucleic acid sequence, thereby producing a combination. The combination is maintained under conditions in which the target nucleic acid is amplified, thereby generating amplicons of the target nucleic acid sequence wherein one or more of the amplicons comprise one or more of the modified (e.g., methylated) nucleotides. The amplicons are contacted with a restriction enzyme (e.g., a methyl specific restriction enzyme) that digests nucleic acid sequences comprising the modified nucleotides, thereby removing the one or more amplicons which comprise one or more of the modified (e.g., methylated) nucleotides.

In other aspects, the invention is directed to a method of amplifying a target nucleic acid sequence. The method comprises contacting the target nucleic acid sequence with native nucleotides, a nucleic acid polymerase, and one or more primers wherein each primer is complementary to a portion of the target nucleic acid sequence and comprises one or more modified (e.g., methylated) nucleotides, thereby producing a combination. The combination is maintained under conditions in which the target nucleic acid is amplified, thereby generating amplicons of the target nucleic acid sequence wherein one or more of the amplicons comprise one or more modified (e.g., methylated) nucleotides. The amplicons are contacted with a restriction enzyme (e.g., a methyl specific restriction enzyme), thereby removing all or a portion of the primers from the one or more amplicons which comprise one or more of the modified (e.g., methylated) nucleotides.

In other aspects, the invention is directed to a method of replicating a single stranded oligo or DNA library. The method comprises ligating a first amplification primer to the single stranded oligo library or DNA library thereby forming a ligation product. The ligation product is contacted with a modified (e.g., methylated) primer that hybridizes to the first amplification primer and a polymerase, thereby forming a combination. The combination is maintained under conditions in which a reverse complement of the single stranded oligo or DNA is generated. A second amplification primer is ligated to the reverse complement, thereby producing a double adapted ligation product sequence. The double adapted litigation product is contacted with native nucleotides, a nucleic acid polymerase, and one or more primers wherein each primer is complementary to a portion of the double adapted litigation product sequence and comprises one or more modified (e.g., methylated) nucleotides, thereby producing a combination. The combination is maintained under conditions in which the double adapted litigation product is amplified, thereby generating amplicons of the double adapted litigation product sequence wherein one or more of the amplicons comprise one or more of the modified (e.g., methylated) nucleotides. The amplicons are contacted with a restriction enzyme (e.g., a methyl specific restriction enzyme) that cleaves nucleotide sequences comprising one or more of the modified nucleotides, thereby removing all or a portion of the primers from the one or more amplicons which comprise one or more modified (e.g., methylated) nucleotides.

BRIEF DESCRIPTION OF THE DRAWINGS

FIGS. 5A-5C: 5A shows results of PCR with uracil replacement; 5B sows results of PCR control with native dNTPs; 5C shows results of digestion with UDG, FpG (sample 1=no UTP, sample 2=dUTP library.

FIG. 15: Secondary PCR of Nextera libraries using 5me-dCTP (Green, Turqoise) and 5hme-dCTP (Red, Blue). 16.6 kb amplicons were fragmented with Nextera at 55° C. for 30 minutes. Subsequent PCR utilized 12 cycles of amplification using Q5 polymerase (NEB) with additional nucleotides spiked in.

DETAILED DESCRIPTION OF THE INVENTION

Figure 1:
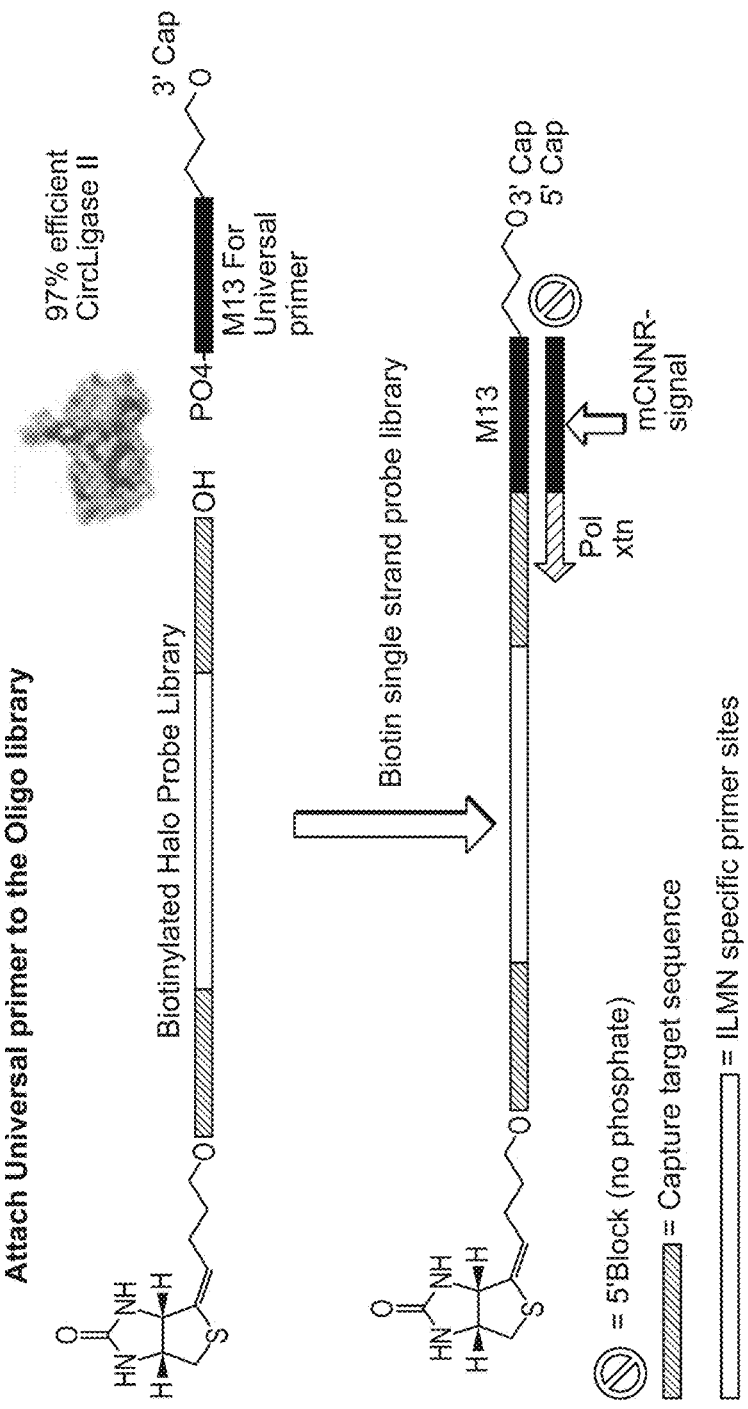
FIG. 1: A biotinylated probe library often used in exome capture or targeted sequencing is represented. 3' OH is targeted with a single stranded DNA Ligase like Circligase I or Circligase II (Epicentre) or Mth Ligase (NEB). A Universal Primer with a 3' cap is ligated to the probe library. The cap is required to prevent Primer to Primer ligation.
Figure 2:
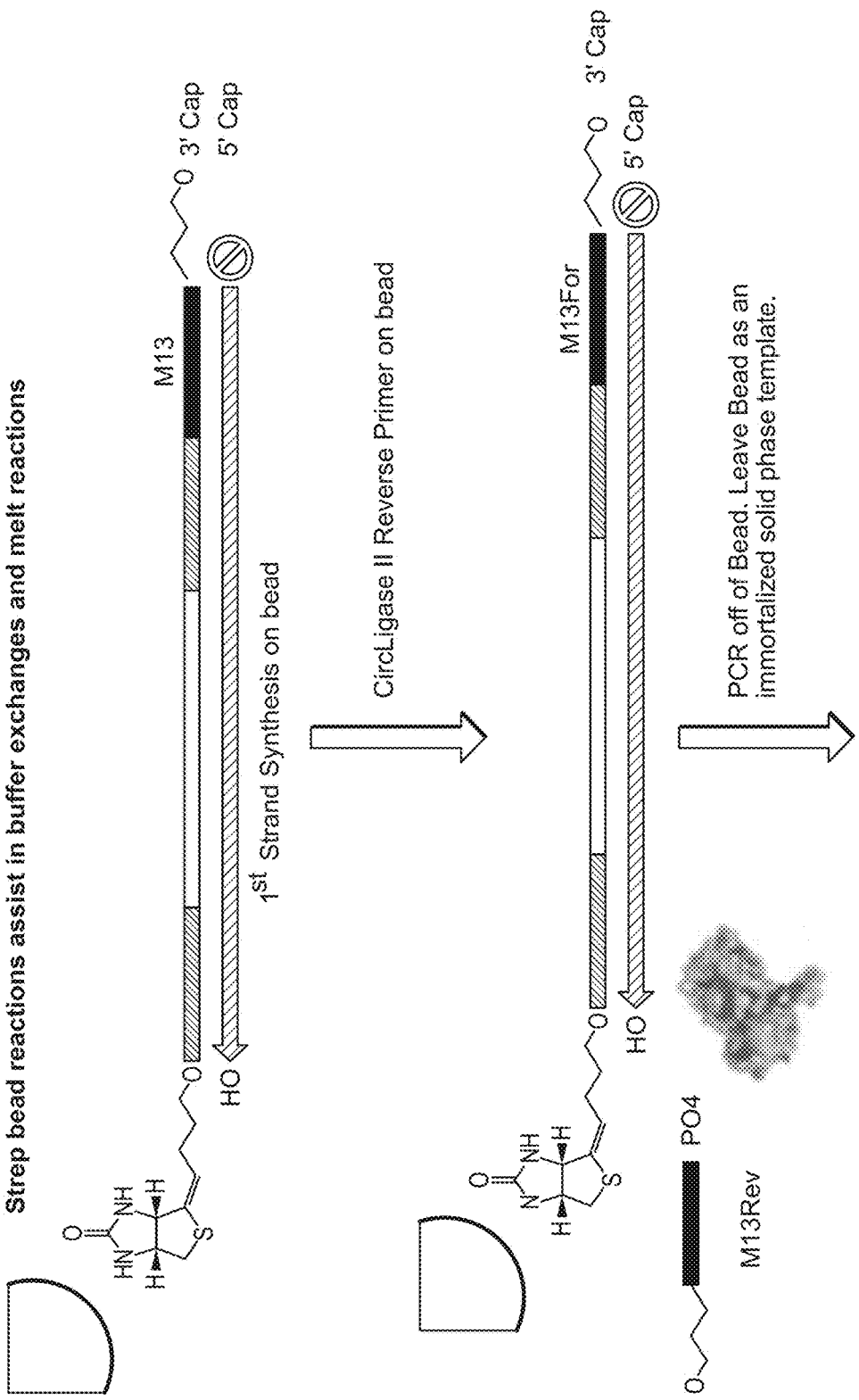
FIG. 2: 2nd Strand synthesis is performed with the complement to the M13 universal primer with a methylated CNNR signal for subsequent MspJI digestion. Polymerase extension double strands the probe library and leaves only one 3' OH which can targeted with the 2nd Ligation step. Once this final ligation step is complete, PCR with Methylated primers can be performed. This shares some similarities with 5 prime independent cloning described by Pak and Fire but has the added benefit of being able to subsequently remove the amplification primers to bring the oligo library back to its native state after amplification.
Figure 3:
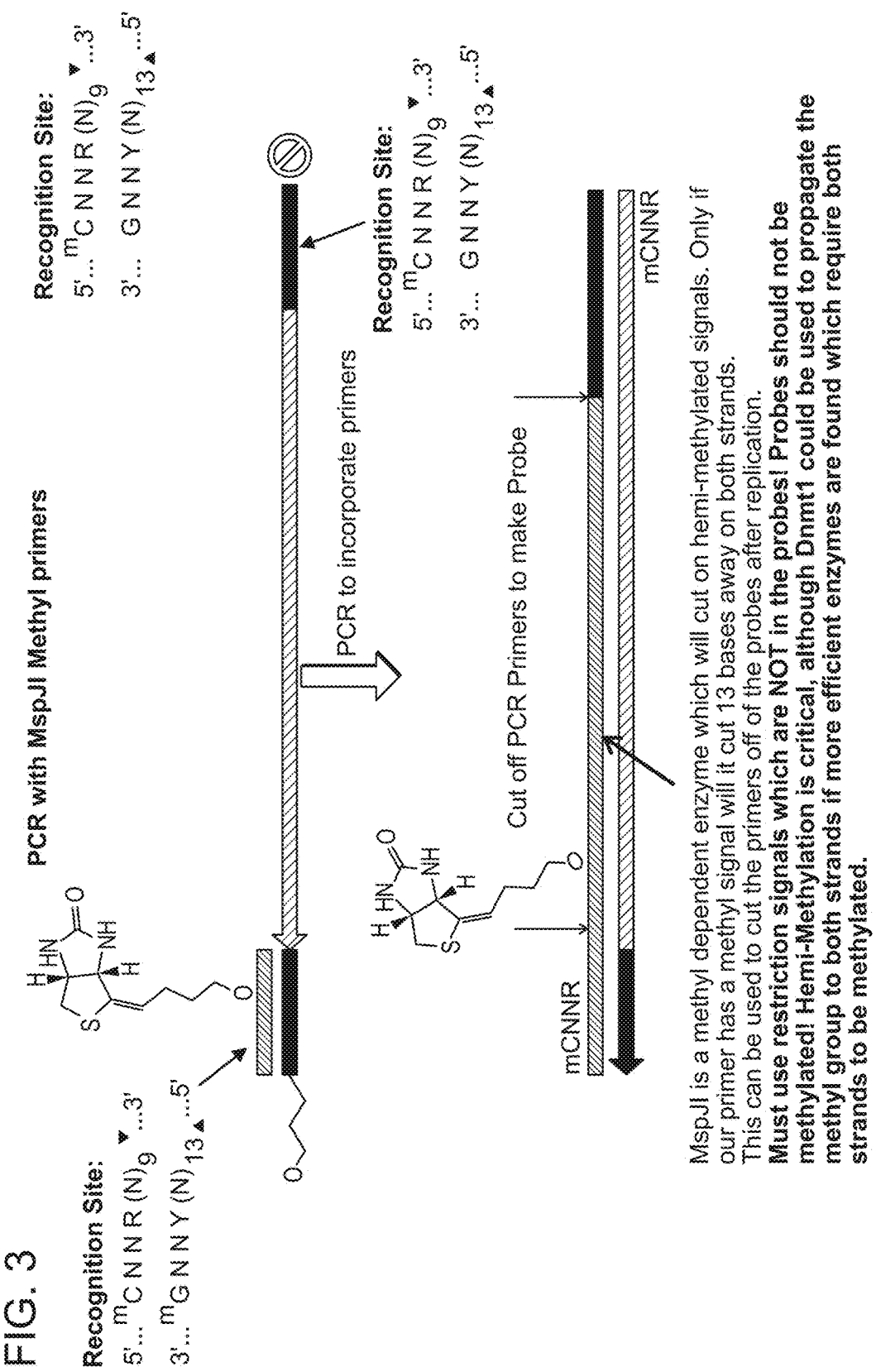
FIG. 3: Representation of an oligo Library after amplification. It has 2 methylated CNNR signals in the PCR primers. It has an optional Biotin that can help to single strand the oligo library after amplification. It has no internal methylation signals (green arrow) in this embodiment but PCR with methylCTP is an option for decontamination procedures. The blue arrows represent the cut sites after amplification and digestion by MspJI.
Figure 4:
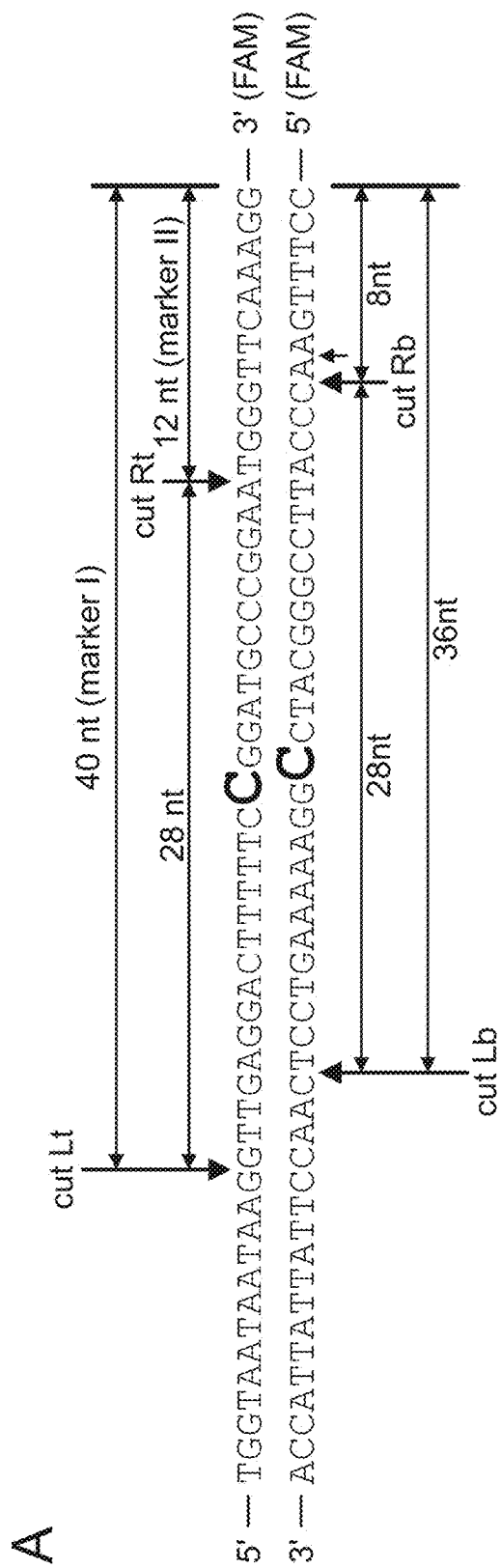
FIG. 4: Depiction of the MspJI restriction activity (SEQ ID NOs: 1 and 2) as described by Zheng et al. Nucleic Acids Res 38(16): 5527-5534.

A description of example embodiments of the invention follows.

Universal primers are utilized in many clinical PCR applications. A side effect of universal primers is that subsequent PCR reaction setups are easily contaminated with PCR products from a previous amplification reaction. Clinical laboratories have traditionally utilized dUTP in PCR to generate PCR products that are different from genomic DNA and are specifically cleavable with uracil DNA glycosylase (UDG).

To address the issues associated with decontamination methods for nucleic acid (e.g., DNA; RNA), the use of a single cycle of primer extension with adenosine (A), cytosine (C), guanine (G) and thymine (T) instead or uracil (U) will generate hemi-uracilyated amplicons where the Watson strand is void of uracils while the Crick strand remains uracilyated. The first step in seeding the DNA cluster PCR requires denaturation (e.g., NaOH denaturization) where the Watson strand can operate independently of the Crick strand and be utilized successfully in cluster PCR. This delivers a clinical sequencing pipeline that is congruent with UDG decontamination methods. Using these methods, only the PCR products that contain uracil are enzymatically digested therefore any contaminating PCR products can be digested with no risk to digesting the target DNA about to be amplified. Unfortunately, uracilated DNA is not amplified well with widely-used emulsion or cluster PCR kits, due to the use of uracil-illiterate polymerases in most next generation sequencing platforms.

To address the issues associated with amplification methods using uracilated DNA, in one aspect, the invention provides for use of one or more modified (e.g., methylated) deoxynucleotide triphosphates (dNTPs) (e.g., deoxycytidine triphosphate (dCTP) such as methyl dCTP (5-methyl dCTP; and 5-hydroxymethyl cystine) or methylated primers (e.g., a primer comprising methylated nucleotides) in conjunction with methyl specific restriction enzymes, e.g., MspJ1 (New England Biolabs) (Zheng et al) to amplify a target nucleic acid sequence and/or remove amplicons of a target nucleic acid sequence after amplification of the target nucleic acid sequence. The benefits of using methylated dNTPs is that it is incorporated more readily and with less error than dUTP and several antibodies and methyl binding proteins are commercially available to isolate methylated PCR products from non-methylated PCR products. Examples and methods are described within demonstrating the success of each of these techniques.

In some aspects, described herein is a decontamination ready encoded amplification, referred to herein as "DREAM PCR", that replaces this uracil base with methylcytosine, as most polymerases are methylcytosine literate and efficiently incorporate this base into a PCR product (REF). In other aspects, in addition to 5-methylcytosine, the recently described "6th base" 5-hydroxymethylcytosine and the enzymes that exist which differentially digest or capture hydroxymethylated cytosine are used. As described herein, techniques that detect modified bases such as 5-hydroxymethylcytosine from 5-methylcytosine, and that moreover, differentially detect 5-hydroxymethylcytosine from 5-methylcytosine provide for improved amplification methods.

To enable selective serial digestion of the two nucleotides, DREAM PCR substitutes the methyl-specific endonuclease MspJI in place of UDG. MspJI digests heavily methylated PCR products differentially than lightly methylated substrate genomic DNA and it has a preference for digesting double stranded methylated DNA over single stranded lightly methylated circular gDNA presented with a Haloplex exome capture system (McKernan in press). Incorporation of 5-hydroxymethylcytosine enables serial PCR steps to be performed each with a different 5th base and each respectively digestable with unique enzymes (MspJI and AbaSI). This offers unique decontamination solutions for more complex massively parallel DNA sequencing workflows requiring more than one amplification step.

Accordingly, in some aspects, the invention is directed to a method of removing amplicons of non target nucleic acid having one or more modified (e.g., methylated) nucleotides from a sample wherein the sample comprises the non target nucleic acid and a target nucleic acid sequence to be amplified. The method comprises contacting the sample with a composition comprising a restriction enzyme that cleaves (e.g., specifically (selectively) cleaves (recognizes)) a nucleic acid sequence comprising the modified nucleotide(s) (e.g., a methyl specific restriction enzyme) and that is capable of being deactivated, thereby producing a combination; maintaining the combination under conditions in which the amplicons of the non target nucleic acid are digested by the restriction enzyme (e.g., methyl specific restriction enzyme) prior to amplification of the target nucleic acid; and amplifying the target nucleic acid sequence thereby producing amplicons of the target nucleic acid sequence, and thereby removing the amplicons of the non target nucleic acid from the sample comprising the target nucleic acid sequence to be amplified. The composition can further comprise (i) deoxynucleotide triphophates (dNTPs) comprising dATP, dTTP, dGTP, and dCTP (ii) a nucleic acid polymerase, (iii) one or more primers that is complementary to a portion of the target nucleic acid sequence.

In a particular aspect, the invention is directed to a method of removing amplicons of non target nucleic acid having one or more methylated nucleotides from a sample wherein the sample comprises the non target nucleic acid and a target nucleic acid sequence to be amplified. The method comprises contacting the sample with a composition comprising a methyl specific restriction enzyme that is capable of being deactivated, thereby producing a combination; maintaining the combination under conditions in which the amplicons of the non target nucleic acid are digested by the methyl specific restriction enzyme prior to amplification of the target nucleic acid; and amplifying the target nucleic acid sequence thereby producing amplicons of the target nucleic acid sequence, and thereby removing the amplicons of the non target nucleic acid from the sample comprising the target nucleic acid sequence to be amplified. The composition can further comprise (i) deoxynucleotide triphophates (dNTPs) comprising dATP, dTTP, dGTP, and dCTP (ii) a nucleic acid polymerase, (iii) one or more primers that is complementary to a portion of the target nucleic acid sequence. The method can further comprise contacting the amplicons of the target nucleic acid sequence with a (second, active) methyl specific restriction enzyme, thereby producing a combination (a second combination) and maintaining the combination under conditions in which the amplkcons of the target nucleic acid sequence are digested. The methyl specific restriction enzyme that is contacted with the amplicons of the target nucleic acid sequence can be identical to the methyl specific restriction enzyme that is contacted with the amplicons of the non target nucleic acid sequence or can be a different methyl specific restriction enzyme than the methyl specific restriction enzyme that is contacted with the amplicons of the non target nucleic acid sequence. The method can further comprise contacting the amplicons of the target nucleic acid sequence with a methyl specific restriction enzyme prior to amplification of a second target nucleic acid.

In other aspects, the invention is directed to a method of serially amplifying a target nucleic acid sequence wherein the first amplification is performed with a first cleavable base and a subsequent (e.g., second, third fourth, fifth, etc.) amplification is performed with a second cleavable base, and the first cleavable base and the second cleavable base are different. In some aspects, the first cleavable base is cleaved by a first restriction enzyme and the second cleavable base is a uniquely cleavable base that is cleaved by a second restriction enzyme that specifically cleaves amplicons comprising the uniquely cleavable base; the subsequent amplification is performed with the uniquely cleavable base and the second restriction enzyme; and the first amplification is performed with the first cleavable base wherein amplicons comprising the first cleavable base can be simultaneously cleaved with the first restriction enzyme that cleaves the different cleavable base. The method can further comprise contacting the target nucleic acid sequence with (i) deoxynucleotide triphophates (dNTPs) comprising dATP, dTTP, dGTP, and dCTP (ii) a nucleic acid polymerase, (iii) one or more primers that is complementary to a portion of the target nucleic acid sequence.

In another aspect, the invention is directed to a method of serially amplifying a target nucleic acid sequence wherein the first amplification is performed with a first cleavable base and a subsequent (e.g., a second, third, fourth, fifth, etc.) amplification is performed with a second cleavable base, and the first cleavable base and the second cleavable base are different. That is, the cleavable bases differ in that when present in a nucleic acid sequence (e.g., an amplicon) a first cleavable base is cleaved by one (e.g., a first) restriction enzyme and the second cleavable base is cleaved by another (e.g., second, distinct) restriction enzyme. The method can further comprise contacting the target nucleic acid sequence with (i) deoxynucleotide triphophates (dNTPs) comprising dATP, dTTP, dGTP, and dCTP (ii) a nucleic acid polymerase, (iii) one or more primers that is complementary to a portion of the target nucleic acid sequence.

In addition, the method can comprise contacting the target nucleic acid with a composition comprising (i) deoxynucleotide triphophates (dNTPs) comprising dATP, dTTP, dGTP, and dCTP wherein one or more of the deoxynucleotide triphophates comprise the first cleavable base (ii) a nucleic acid polymerase, (iii) one or more primers that are complementary to a portion of the target nucleic acid sequence, and (iv) the first restriction enzyme wherein the first restriction enzyme is capable of being deactivated, thereby producing a combination; and maintaining the combination under conditions in which nucleic acid sequences comprising the first cleavable base are digested by the first restriction enzyme prior to amplification of the target nucleic acid. The method can further comprise amplifying the target nucleic acid sequence under conditions in which amplicons of the target nucleic acid sequence have one or more of the first cleavable base; contacting the amplicons of the target nucleic acid sequence with a composition comprising (i) deoxynucleotide triphophates (dNTPs) comprising dATP, dTTP, dGTP, and dCTP wherein one or more of the deoxynucleotide triphophates comprise the second cleavable base (ii) a nucleic acid polymerase, (iii) one or more primers that are complementary to a portion of the target nucleic acid sequence, and (iv) the second restriction enzyme that is capable of being deactivated and that selectively digests nucleic acid sequences comprising the second cleavable base; maintaining the combination of b) under conditions in which nucleic acid sequences comprising the second cleavable base are digested by the second restriction enzyme prior to amplification of the target nucleic acid; and amplifying the target nucleic acid sequence, thereby producing amplicons of the target nucleic acid sequence comprising the first cleavable base and the second cleaveable base. The first cleavable base can be methylated dCTP and the first restriction enzyme is MspJI.

In other aspects, the invention is directed to a method of removing amplicons of non target nucleic acid having one or more nucleotides that are modified (e.g., methylated) from a sample wherein the sample comprises the non target nucleic acid and a target nucleic acid sequence to be serially amplified. The method comprises contacting the sample with a composition (a first composition) comprising (i) deoxynucleotide triphophates (dNTPs) comprising dATP, dTTP, dGTP, and dCTP wherein one or more of the deoxynucleotide triphophates are modified (e.g., modified with a first moiety, e.g., methylated with a first methyl group) (ii) a nucleic acid polymerase, (iii) one or more primers that are complementary to a portion of the target nucleic acid sequence, and (iv) a first restriction enzyme (e.g., a (first) methyl specific restriction enzyme) that is capable of being deactivated and that digests nucleic acid sequences comprising nucleotides modified with the first moiety (e.g., that are methylated with the first methyl group), thereby producing a combination (a first combination). The combination is maintained under conditions in which the amplicons of the non target nucleic acid are digested by the first restriction enzyme (e.g., a methyl specific restriction enzyme) prior to amplification of the target nucleic acid. The target nucleic acid sequence is amplified, thereby producing amplicons of the target nucleic acid sequence having one or more modified nucleotides comprising the first moiety (e.g., nucleotides that are methylated with the first methyl group). The amplicons of the target nucleic acid sequence are then subsequently (serially) amplified by contacting the amplicons with a composition (second composition) comprising (i) deoxynucleotide triphophates (dNTPs) comprising dATP, dTTP, dGTP, and dCTP wherein one or more of the deoxynucleotide triphophates are modified (e.g., modified with a second moiety, e.g., methylated with a second methyl group), (ii) a nucleic acid polymerase, (iii) one or more primers that are complementary to a portion of the target nucleic acid sequence, and (iv) a second restriction enzyme (e.g., a (second) methyl specific restriction enzyme) that is capable of being deactivated and that selectively digests nucleic acid sequences comprising nucleotides modified with the second moiety (e.g., that are methylated with the second methyl group), thereby producing a combination (a second combination). The combination is maintained under conditions in which the amplicons of the non target nucleic acid are digested by the second restriction enzyme (e.g., the second methyl specific restriction enzyme) prior to the subsequent amplification of the target nucleic acid. The target nucleic acid sequence is amplified, thereby producing amplicons of the target nucleic acid sequence having one or more nucleotides modified with the first moiety and the second moiety (amplicons of the target nucleic acid sequence that are methylated with the first methyl group and the second methyl group), thereby removing amplicons of the non target nucleic acid having one or more nucleotides that are modified (e.g., methylated) from a sample wherein the sample comprises the non target nucleic acid and a target nucleic acid sequence to be serially amplified.

In other aspects, the invention is directed to a method of removing amplicons of non target nucleic acid having one or more nucleotides that are methylated from a sample wherein the sample comprises the non target nucleic acid and a target nucleic acid sequence to be serially amplified. The method comprises contacting the sample with a composition (a first composition) comprising (i) deoxynucleotide triphophates (dNTPs) comprising dATP, dTTP, dGTP, and dCTP wherein one or more of the deoxynucleotide triphophates are methylated with a first methyl group (ii) a nucleic acid polymerase, (iii) one or more primers that are complementary to a portion of the target nucleic acid sequence, and (iv) a first methyl specific restriction enzyme that is capable of being deactivated and that digests nucleic acid sequences comprising nucleotides that are methylated with the first methyl group, thereby producing a combination (a first combination). The combination is maintained under conditions in which the amplicons of the non target nucleic acid are digested by the first methyl specific restriction enzyme prior to amplification of the target nucleic acid. The target nucleic acid sequence is amplified, thereby producing amplicons of the target nucleic acid sequence having one or more nucleotides that are methylated with the first methyl group. In a subsequent amplification of the target nucleic acid sequence, the amplicons of the target nucleic acid sequence are contacted with a composition (second composition) comprising (i) deoxynucleotide triphophates (dNTPs) comprising dATP, dTTP, dGTP, and dCTP wherein one or more of the deoxynucleotide triphophates are methylated with a second methyl group (ii) a nucleic acid polymerase, (iii) one or more primers that are complementary to a portion of the target nucleic acid sequence, and (iv) a second methyl specific restriction enzyme that is capable of being deactivated and that selectively digests nucleic acid sequences comprising nucleotides that are methylated with the second methyl group, thereby producing a combination (a second combination). The combination is maintained under conditions in which the amplicons of the non target nucleic acid are digested by the second methyl specific restriction enzyme prior to amplification of the target nucleic acid. The target nucleic acid sequence is amplified, thereby producing amplicons of the target nucleic acid sequence having one or more nucleotides that are methylated with the first methyl group and the second methyl group, thereby removing amplicons of the non target nucleic acid having one or more nucleotides that are methylated from a sample wherein the sample comprises the non target nucleic acid and a target nucleic acid sequence to be serially amplified.

In some aspects of the method the dNTP methylated with the first methyl group is methylated dCTP and the first methyl specific restriction enzyme is MspJI. In other aspects of the method, the dNTP methylated with the second methyl group is hydroxymethylated dCTP and the second methyl specific restriction enzyme is AbaSI.

In other aspects, the invention is directed to a method of removing amplicons of a target nucleic acid sequence after amplification of the target nucleic acid sequence. The method comprises contacting the target nucleic acid sequence with (i) deoxynucleotide triphophates (dNTPs) comprising dATP, dTTP, dGTP, and dCTP wherein one or more of the deoxynucleotide triphophates are modified (e.g., methylated) (ii) a nucleic acid polymerase, and (iii) one or more primers that are complementary to a portion of the target nucleic acid sequence, thereby producing a combination. The combination is maintained under conditions in which the target nucleic acid is amplified, thereby generating amplicons of the target nucleic acid sequence wherein one or more of the amplicons comprise one or more of the modified (e.g., methylated) nucleotides. The amplicons are contacted with a restriction enzyme (e.g., a methyl specific restriction enzyme) that digests nucleic acid sequences comprising the modified nucleotides, thereby removing the one or more amplicons which comprise one or more of the modified (e.g., methylated) nucleotides.

In other aspects, the invention is directed to a method of removing amplicons of a target nucleic acid sequence after amplification of the target nucleic acid sequence. The method comprises contacting the target nucleic acid sequence with (i) deoxynucleotide triphophates (dNTPs) comprising dATP, dTTP, dGTP, and dCTP wherein one or more of the deoxynucleotide triphophates are methylated (ii) a nucleic acid polymerase, and (iii) one or more primers that are complementary to a portion of the target nucleic acid sequence, thereby producing a combination. The combination is maintained under conditions in which the target nucleic acid is amplified, thereby generating amplicons of the target nucleic acid sequence wherein one or more of the amplicons comprise one or more methylated nucleotides. The amplicons are contacted with a methyl specific restriction enzyme, thereby removing the one or more amplicons which comprise one or more methylated nucleotides.

In other aspects, the invention is directed to a method of amplifying a target nucleic acid sequence. The method comprises contacting the target nucleic acid sequence with native nucleotides (e.g., dATP, dTTP, dCTP, dGTP), a nucleic acid polymerase, and one or more primers wherein each primer is complementary to a portion of the target nucleic acid sequence and comprises one or more modified (e.g., methylated) nucleotides, thereby producing a combination. The combination is maintained under conditions in which the target nucleic acid is amplified, thereby generating amplicons of the target nucleic acid sequence wherein one or more of the amplicons comprise one or more modified (e.g., methylated) nucleotides. In a particular aspect, the primers of the amplicon only or primarily comprise one or more of the modified nucleotides. The amplicons are contacted with a restriction enzyme (e.g., a methyl specific restriction enzyme), thereby removing all or a portion of the primers from the one or more amplicons which comprise one or more of the modified (e.g., methylated) nucleotides.

In other aspects, the invention is directed to a method of amplifying a target nucleic acid sequence. The method comprises contacting the target nucleic acid sequence with native nucleotides, a nucleic acid polymerase, and one or more primers wherein each primer is complementary to a portion of the target nucleic acid sequence and comprises one or more methylated nucleotides, thereby producing a combination. The combination is maintained under conditions in which the target nucleic acid is amplified, thereby generating amplicons of the target nucleic acid sequence wherein one or more of the amplicons comprise one or more methylated nucleotides. In a particular aspect, the primers of the amplicon only or primarily comprise one or more of the methylated nucleotides. The amplicons are contacted with a methyl specific restriction enzyme, thereby removing all or a portion of the primers from the one or more amplicons which comprise one or more methylated nucleotides. In some aspects, each primer comprises one or more methylated cytosines, one or more methylated adenosines or a combination thereof.

In other aspects, the invention is directed to a method of replicating a single stranded oligo or DNA library. The method comprises ligating a first amplification primer to the single stranded oligo library or DNA library thereby forming a ligation product. The ligation product is contacted with a modified (e.g., methylated) primer that hybridizes to the first amplification primer and a polymerase, thereby forming a combination. The combination is maintained under conditions in which a reverse complement of the single stranded oligo or DNA is generated. A second amplification primer is ligated to the reverse complement, thereby producing a double adapted ligation product sequence. The double adapted litigation product is contacted with native nucleotides, a nucleic acid polymerase, and one or more primers wherein each primer is complementary to a portion of the double adapted litigation product sequence and comprises one or more modified (e.g., methylated) nucleotides, thereby producing a combination. The combination is maintained under conditions in which the double adapted litigation product is amplified, thereby generating amplicons of the double adapted litigation product sequence wherein one or more of the amplicons comprise one or more of the modified (e.g., methylated) nucleotides. The amplicons are contacted with a restriction enzyme (e.g., a methyl specific restriction enzyme) that cleaves nucleotide sequences comprising one or more of the modified nucleotides, thereby removing all or a portion of the primers from the one or more amplicons which comprise one or more modified (e.g., methylated) nucleotides.

In other aspects, the invention is directed to a method of replicating a single stranded oligo or DNA library. The method comprises ligating a first amplification primer to the single stranded oligo library or DNA library thereby forming a ligation product. The ligation product is contacted with a methylated primer that hybridizes to the first amplification primer and a polymerase, thereby forming a combination. The combination is maintained under conditions in which a reverse complement of the single stranded oligo or DNA is generated. A second amplification primer is ligated to the reverse complement, thereby producing a double adapted ligation product sequence. The double adapted litigation product is contacted with native nucleotides, a nucleic acid polymerase, and one or more primers wherein each primer is complementary to a portion of the double adapted litigation product sequence and comprises one or more methylated nucleotides, thereby producing a combination. The combination is maintained under conditions in which the double adapted litigation product is amplified, thereby generating amplicons of the double adapted litigation product sequence wherein one or more of the amplicons comprise one or more methylated nucleotides. The amplicons are contacted with a methyl specific restriction enzyme, thereby removing all or a portion of the primers from the one or more amplicons which comprise one or more methylated nucleotides. In some aspects, a template independent DNA ligase is used to ligate methylated amplification primers to the oligo library. In other aspects, the template independent DNA ligase is Mth Ligase. In yet other aspects, each primer comprises one or more methylated cytosines, one or more methylated adenosines or a combination thereof.

As used herein, "amplifying" "amplification" or an "amplification reaction" refers to methods for amplification of a nucleic acid sequence including polymerase chain reaction (PCR), ligase chain reaction (LCR), rolling circle amplification (RCA), strand displacement amplification (SDA) and multiple displacement amplification (MDA), serial amplification as will be understood by a person of skill in the art. Such methods for amplification comprise, e.g., primers that anneal to the nucleic acid sequence to be amplified, a DNA polymerase, and nucleotides. Furthermore, amplification methods, such as PCR, can be solid-phase amplification, polony amplification, colony amplification, emulsion PCR, bead RCA, surface RCA, surface SDA, etc., as will be recognized by one of skill in the art. It will also be recognized that it is advantageous to use an amplification method that results in exponential amplification of free DNA molecules in solution or tethered to a suitable matrix by only one end of the DNA molecule. Methods that rely on bridge PCR, where both PCR primers are attached to a surface (see, e.g., WO/18957 and Adessi et al., Nucleic Acids Research (2000): 28(20): E87) result in only linear amplification, which does not produce sufficient amounts of product to support efficient library construction for subsequent sequencing. Furthermore, the products of bridge PCR technologies are array-bound, and would have to be cleaved from the support as intact double stranded DNA molecules to be useful for subsequent sequencing. In addition, it will be recognized that it is often advantageous to use amplification protocols that maximize the fidelity of the amplified products to be used as templates in DNA sequencing procedures. Such protocols use, for example, DNA polymerases with strong discrimination against misincorporation of incorrect nucleotides and/or strong 3' exonuclease activities (also referred to as proofreading or editing activities) to remove misincorporated nucleotides during polymerization.

The methods provided herein utilize a (one or more) modified bases. As used herein, the term "base" refers to the heterocyclic nitrogenous base of a nucleotide or nucleotide analog (e.g., a purine, a pyrimidine, a 7-deazapurine). A "nucleoside" refers to a nitrogenous base linked to a sugar molecule. A "nucleotide" (e.g., "deoxyribonuleotide (dNTP)", "ribonucleotide") is a nitrogenous heterocyclic base (or nucleobase), which can be either a double-ringed purine or a single-ringed pyrimidine; a five-carbon pentose sugar (deoxyribose in DNA or ribose in RNA); and a phosphate group. Suitable bases for use in the methods of the invention include, but are not limited to, adenine (A) (e.g., dATP), cytosine (C) (e.g., dCTP), guanine (G) (e.g., dGTP), thymine (T) (e.g., dTTP), and uracil (U) (e.g., dUTP). These and other suitable bases will permit a nucleotide bearing the base to be enzymatically incorporated into a polynucleotide chain. The base will also be capable of forming a base pair involving hydrogen bonding with a base on another nucleotide or nucleotide analog. The base pair can be either a conventional (standard) Watson-Crick base pair or a non-conventional (non-standard) non-Watson-Crick base pair, for example, a Hoogstein base pair or bidentate base pair. The terms "base" and "deoxynucleotide triphosphate (dNTP)" are at times used interchangeably.

As used herein, "Watson-Crick base pair" refers to a pair of hydrogen-bonded bases on opposite antiparallel strands of a nucleic acid. The rules of base pairing, which were first elaborated by Watson and Crick, are well known to those of skill in the art. For example, these rules require that adenine (A) pairs with thymine (T) or uracil (U), and guanine (G) pairs with cytosine (C), with the complementary strands anti-parallel to one another. As used herein, the term "Watson-Crick base pair" encompasses not only the standard AT, AU or GC base pairs, but also base pairs formed between non-standard or modified bases of nucleotide analogs capable of hydrogen bonding to a standard base or to another complementary non-standard base. One example of such non-standard Watson-Crick base pairing is the base pairing which involves the nucleotide analog inosine, wherein its hypoxanthine base forms two hydrogen bonds with adenine, cytosine or uracil of other nucleotides.

A "modified base" comprises one or more moieties that renders the base cleavable (a cleavable base) by one or more restriction enzymes. The terms "modified base" and "modified deoxynucleotide triphiosphate" are at times used interchangeably. As will be appreciated by those of skill in the art a restriction enzyme can specifically recognize and cleave a particular cleavable base (e.g., a single cleavable base), or can recognize and cleave more than one cleavable base. A variety of modified bases are known in the art, such as modified purine bases (e.g., Hypoxanthine, Xanthine, 7-Methylguanine, Inosine, Xanthosine, 7-Methylguanosine) and modified pyrimidine bases (e.g., 5,6-Dihydrouracil, 5-Methylcytosine, 5-Hydroxymethylcytosine, Dihydrouridine, 5-Methylcytidine).

In some aspects, the modified base is a methylated, hydroxymethylated, and/or a fomylated base. In one aspect, the modified base is a formylated deoxynucleotide triphophate (dNTP). In other aspects, the modified base is a methylated dNTP. In some aspects, the modified base is a methylated dNTP, a hydroxymethylated dNTP or a combination thereof. In some aspects, the one or more methylated deoxynucleotide triphophates is one or more methylated cytosines, one or more hydroxymethylated dNTPs, one or more methylated adenosines or a combination thereof. In other aspects, the one or more methylated cytosines is 5-methyl cytosine, 5-hydroxymethyl cytosine, or a combination thereof. In yet other aspects, the one or more methylated adenosines is N6 methyl adenosine.

In some aspects, the modified base is used in an amplification reaction. In some aspects, all or some of a (one or more) particular dNTP are modified (e.g., methylated). In other aspects, about 1%, 2%, 5%, 10%, 15%, 20%, 25%, 30%, 35%, 40%, 45%, 50%, 55%, 60%, etc. of a (one or more) particular dNTP are modified. In other aspects, about 25% of a (one or more) particular dNTP are methylated.

As described herein the modified base is cleavable by one or more restriction enzymes. As will be appreciated by those of skill in the art a restriction enzyme can specifically (selectively) recognize and cleave a particular cleavable base (e.g., a single cleavable base) to the exclusion of other cleavablebases, or can recognize and cleave more than one cleavable base. In some aspects, the restriction enzyme digests a nucleic acid sequence at the site of the modified base or at a site (loci) that is distant from the modified base (e.g., 1, 2, 3, 4, 5, 6, 7, 8, 9, 10, 11, 12, 13, 14, 15, 16, 17, 18, 19, 20, 21, 22, etc. bases away from the modified based (e.g., methylated base)). In other aspects, the restriction enzyme can cleave a nucleotide sequence comprising a methylated base (e.g., a methyl specific restriction enzyme), a nucleotide sequence comprising a hydroxymethylated base (e.g., a hydroxymethyl specific restriction enzyme), or a nucleotide sequence comprising methylated bases and hydroxymethylated bases.

In some aspects, the restriction enzyme is capable of being deactivated (e.g., denatured). In some aspects, the restriction enzyme is deactivated upon a change (e.g., increase; decrease) in temperature (e.g., heat labile; cold labile), a change (e.g., increase; decrease) in pH (e.g., pH labile), contact with a reagent (e.g., cofactors which can differentially chelate (EGTA for Ca2+ and EDTA for Mg2+), or a combination thereof. In other aspects, the deactivation of the restriction enzyme is permanent. That is, in some aspects, once the restriction enzyme is deactivated, it cannot be reactivated (e.g., renatured; brought back to its native (active) form). In aspects, in which more than one restriction enzyme is used, the first methyl specific restriction enzyme, the second methyl specific restriction enzyme or both are deactivated upon a change in temperature, a change in pH, contact with a reagent (cofactors which can differentially chelated (EGTA for Ca2+ and EDTA for Mg2+).

As described herein, a sample comprising non target nucleic acid and/or target nucleic acid is contacted with a restriction enzyme that is capable of being deactivated to produce a combination, and the combination is maintained under conditions in which amplicons comprising the modified base which is recognized and cleavable by the restriction enzyme are digested by the restriction enzyme prior to amplification. As is known in the art, many amplification reactions comprise one or more steps that involve an increase in temperature (e.g., to denature a nucleic acid sequence such as double stranded DNA).

Thus, in some aspects, the restriction enzyme used in the methods of the invention is deactivated upon a change in temperature. In a particular aspect, the restriction enzyme is deactivated upon an increase in temperature (e.g., a heat labile restriction enzyme), such as during amplification of a nucleic acid sequence in an amplification reaction. Once the amplification reaction which includes a step that involves an increase in temperature occurs, the restriction enzyme is deactivated. Thus, after amplification, amplicons which comprise the modified base which is recognized and cleavable by the restriction enzyme will not be digested by the restriction enzyme since it is longer active.

In some aspects, the methyl specific restriction enzyme is MspJ1, FspE1, LpnPI, AspBHI, RlaI, SgrTI, AbaSI or a combination thereof.

As described herein, amplification or extension of a primer (e.g., DNA synthesis) can be accomplished using a nucleic acid polymerase which is capable of enzymatically-incorporating both standard (dNTPs) and modified thiol deoxynucleotides (sdNTPs) into a growing nucleic acid strand. As used herein, the phrase a "nucleic acid polymerase" or "nucleic acid polymerase enzyme" refers to an enzyme (e.g., naturally-occurring, recombinant, synthetic) that catalyzes the template-dependent polymerization of nucleoside triphosphates to form primer extension products that are complementary to one of the nucleic acid strands of the template nucleic acid sequence. Numerous nucleic acid polymerases are known in the art and are commercially available. In some aspects, the nucleic acid polymerases that are thermostable, i.e., they retain function after being subjected to temperatures sufficient to denature annealed strands of complementary nucleic acids.

Suitable polymerases for the methods of the present invention include any polymerase known in the art to be useful for recognizing and incorporating standard deoxynucleotides. Examples of such polymerases are disclosed in Table 1 of U.S. Pat. No. 6,858,393, the contents of which are incorporated herein by reference. Many polymerases are known by those of skill in the art to possess a proof-reading, or exonucleolytic activity, which can result in digestion of 3' ends that are available for primer extension. In order to avoid this potential problem, it may be desirable to use polymerase enzyme which lack this activity (e.g., exonuclease-deficient polymerases, referred to herein as exo- polymerases). Such polymerases are well known to those of skill in the art and include, for example, Klenow fragment of *E. Coli* DNA polymerase I, Sequenase, exo-*Thermus aquaticus* (Taq) DNA polymerase and exo-*Bacillus stearothermophilus* (Bst) DNA polymerase. In a particular embodiment, incorporation of deoxynucleotides, including modified deoxynucleotides (dNTPs), into a growing nucleic acid strand (e.g., DNA) is accomplished using a nucleic acid amplification reaction, such as PCR. Therefore, especially suitable polymerases for the methods of the present invention include those that are stable and function at high temperatures (i.e., thermostable polymerases useful in PCR thermal cycling). Examples of such polymerases include, but are not limited to, *Thermus aquaticus* (Taq) DNA polymerase, TaqFS DNA polymerase, thermosequenase, Therminator DNA polymerase, Tth DNA polymerase, Pfu DNA polymerase, Q5 polymerase (New England Biolabs), and Vent (exo-)DNA polymerase. In another embodiment, incorporation of triphosphates into RNA is accomplished using an RNA polymerase. Examples of RNA polymerases include, but are not limited to, *E. coli* RNA polymerase, T7 RNA polymerase and T3 RNA polymerases.

The amplification reaction can further comprise one or more reagents that alters the nucleic acid's melting temperature. In some aspects, the one or more reagents comprises dimethyl sulfoxide (DMSO) Tri-methyl glycine (Betaine) or a combination thereof.

As used herein, the phrase "target nucleic acid sequence" or "target nucleotide sequence" can be any nucleotide sequence for which it is desirable to obtain sequence information. As used herein, the term "nucleotide sequence" (target nucleotide sequence; non target nucleotide sequence) refers to a nucleic acid molecule (e.g., DNA, RNA) that is produced by the incorporation of two or more nucleoside triphosphates into a single molecule via one or more covalent linkages (e.g., a phosphodiester bond, a phosphorothiolate linkage). A "target nucleotide sequence" can be any nucleotide sequence for which it is desirable to produce or to obtain sequence information using the methods described herein. The target nucleic acid sequence may be a polynucleotide or oligonucleotide sequence and may be single-stranded or double-stranded. Typically, when a target nucleic acid sequence is initially provided in double-stranded form, the two strands subsequently will be separated (e.g., the DNA will be denatured). The target nucleic acid sequence also may be naturally-occurring, isolated or synthetic. Examples of suitable target nucleic acid sequence include, but are not limited to, genomic DNA, mitochondrial DNA, complementary DNA (cDNA), a PCR product and other amplified nucleotides. RNA may also be used as a target nucleic acid sequence. For example, RNA can be reverse transcribed to yield cDNA, using methods known in the art such as RT-PCR. The target nucleic acid sequence may be used in any convenient form, according to techniques known in the art (e.g., isolated, cloned, amplified), and may be prepared for the sequencing reaction, as desired, according to techniques known in the art. In a particular embodiment, the target nucleic acid sequence comprises DNA. In a further embodiment, the target nucleic acid sequence comprises a sense DNA strand and an antisense DNA strand, wherein at least one primer is annealed to each strand. The non target nucleic acid, the target nucleic acid or both is single stranded, double stranded or a combination thereof. Examples of nucleic acid sequence include a nucleic acid library (e.g., RNA-Seq library, Chip-Seq library, miRNA library, Hi-C library), genomic nucleic acid, mitochondrial nucleic acid or a combination thereof.

A nucleotide sequence can be obtained from any of a variety of sources. For example, DNA or RNA may be isolated from a sample, which may be obtained or derived from a subject.

The word "sample" is used in a broad sense to denote any source of a nucleotide sequence on which sequence determination is to be performed. The source of a sample may be of any viral, prokaryotic, archaebacterial, or eukaryotic species. The sample may be blood or another bodily fluid containing cells; sperm; and a biopsy (e.g., tissue) sample, among others.

As used herein, the term "primer" refers to an oligonucleotide, which is capable of acting as a point for the initiation of synthesis of a primer extension product that is complementary to the template polynucleotide sequence. The primer may occur naturally, as in a purified restriction digest, or be produced synthetically. The appropriate length of a primer depends on the intended use of the primer, but typically ranges from about 5 to about 100; from about 5 to about 75; from about 5 to about 50; from about 10 to about 35; from about 18 to about 22 nucleotides. A primer need not reflect the exact sequence of the template but must be sufficiently complementary to hybridize with a template for primer elongation to occur, i.e., the primer is sufficiently complementary to the template polynucleotide sequence such that the primer will anneal to the template under conditions that permit primer extension. As used herein, the phrase "conditions in which the target nucleic acid sequence is amplified" or "conditions that permit primer extension" refers to those conditions, e.g., salt concentration (metallic and non-metallic salts), pH, temperature, and necessary cofactor concentration, among others, under which a given polymerase enzyme catalyzes the extension of an annealed primer. Conditions for the primer extension activity of a wide range of polymerase enzymes are known in the art. As one example, conditions permitting the extension of a nucleic acid primer by Taq polymerase include the following (for any given enzyme, there can and often will be more than one set of such conditions): reactions are conducted in a buffer containing 50 mM KCl, 10 mM Tris (pH 8.3), 4 mM MgCl2, (200 mM of one or more dNTPs and/or a chain terminator may be included, depending upon the type of primer extension or sequencing being performed); reactions are performed at 72° C.

It will be clear to persons skilled in the art that the size of the primer and the stability of hybridization will be dependent to some degree on the ratio of A-T to C-G base pairings, since more hydrogen bonding is available in a C-G pairing. Also, the skilled person will consider the degree of homology between the extension primer to other parts of the amplified sequence and choose the degree of stringency accordingly. Guidance for such routine experimentation can be found in the literature, for example, Molecular Cloning: a laboratory manual by Sambrook, J., Fritsch E. F. and Maniatis, T. (1989).

Conditions for amplification will vary depending upon the type of sequence being amplified and the type of amplification being used. Examples of conditions under which an amplification reaction is maintained in order to amplify a nucleic acid sequence include one or more amplification cycles which comprises 98° C. for 20 seconds, 60° C. for 15 seconds, 72° C. for 60 seconds; 12° C. for 60 seconds, 98° C. for 20 seconds, 60° C. for 15 seconds, 72° C. for 60 seconds, 12 sequencing cycles at 98° C. for 20 seconds, 72° C. for 3 minutes; an initial 1 minute denaturization at 94° C. followed by 30 cycles of 98° C. at 10 s, 68° C. for 15 minutes; performance of a final 72° C. 10 minute extension prior to 4° C. hold; 12 Cycles of 72° C. for 3 minutes, 98° C. for 30 seconds, 12 cycles of 98° C. for 10 seconds, 63° C. for 30 seconds, 72° C. for 1 minute. In some aspects, the amplification reaction can comprise a heat kill which is followed by a Phi-29 isothermal incorporation (e.g., 80° C./20 minutes to heat kill the MspJI/AbaSI and then add Phi29 for methylated isothermal amp at 37° C., Bst polymerase isothermal amps In some aspects, deoxyinosine triphosphate (dITP) is used in conjunction with Endonuclease VIII which specifically cleaves Inosine.

In addition to decontamination, the hemi-stranding aspects can be used to sequence specific strands of a library.

Methods that use digestible nucleotides have been described (Hartley and Rashtchian 1993). If one desires to replicate a library of single stranded DNA (e.g., an oligo pool) but needed to remove any required PCR primer sites required for amplification, deoxyuridine triphosphate (dUTP) and dITP nucleotides are poor choices as they will be incorporated into the amplicon randomly and not be constrained to the primer sequences. Uracil or inosine could also be sequenced into the primer sequences but these cleavage signals would not be replicated in PCR on subsequent PCR cycles as polymerases incorporate native nucleotides over these bases in PCR. Additionally, these cleavage signals direct enzymes that only cleave one strand of DNA leaving an overhang that needs subsequent and careful end repair. The use of double stranded restriction enzymes has been described but due to the larger (4-20 base pair) recognition signals in restriction enzymes, its not always possible to have a restriction enzyme manage the cleavage of all amplification primers. In addition there is always the concern of the restriction enzyme digesting the target sequence to be amplified. A signal would preferably have a small recognition signal (1-2 bases), cleave both strands preferably remotely, have affinity for various laboratory capture reagents, and be specific for the primer sequences and non-existent in any target sequence.

As described herein, modified bases (e.g., methyl dCTP) in conjunction with restriction enzymes that cleave the modified bases (e.g., MspJI) uniquely meets these requirements and differs from other amplification techniques. In one aspect, target sequences are amplified with transliterated sequence identity which provides for easy decontamination techniques.

An aspect of the methods provided herein is exemplified using methyl-dCTP as a replacement for dCTP. Previously, Wong et al described PCR with 5-methyl-dCTP to screen for "methyl sensitive restriction endonucleases" which were used to screen for restriction endonucleases activities which were blocked by the presence of a methylated cytosine (Wong and McClelland 1991). However, at the time of Wong, "methyl specific restriction enzymes", also known as "methyl dependent restriction enzymes", had not been discovered (Cohen-Karni et al.; Horton et al.; Zheng et al.).

Described herein is the use of the methyl dependent enzymes (e.g., MspJI, AbaSI enzyme) in combination with one or more methylated dNTPS (e.g., 5-methyl-dCTP; 5-hydroxymethyl dCTP) for amplification methods such as PCR. The methods described herein can be used as a replacement for UNG. One benefit of a methylated dNTP embodiment over the use of uracil is that more polymerases are literate with methylated dNTP. Additionally, enzymes like Dnmtl exist which can replicate the methyl group onto the opposite strand if optionally required. Additionally, enzymes such as MspJI are a single enzyme system which can digest DNA on both strands with a single methylated cytosine signal and will not digest DNA with unmethylated cytosine.

In contrast, UNG only removes the Uracil nucleobase by digesting the glycosic bond and thus requires other enzymes such as Endo8 to excise the ribose, and polynucleotide kinase to remove phosphates. After using 3 enzymes one is still only left with a single stranded digestion and one must remove the other strand with T7 exonuclease.

In another aspect, the invention is directed to a method, referred to herein as "Ephemeral Primer Amplification" or EPA, in which methyl dCTP and MspJI are used to replicate oligo libraries.

Oligonucleotides are staples in the DNA diagnostic and DNA sequencing fields. Exome sequencing requires synthesizing 100s to 100,000s oligonucleotides to use as baits for capturing targeted regions of DNA for sequencing. DNA synthesis costs are still expensive often costing several dollars per oligonucleotide. For this reason there exists a need to immortalize or amplify an oligonucleotide (or Probe) library.

Traditional approaches to amplification utilize PCR or Rolling Circle Amplification (RCA). All amplification techniques require PCR primer sequences. These additional PCR primer sites are unwanted DNA sequences on the oligonucleotides probes.

Also described herein is a method to attach universal PCR primer sites to ssDNA oligos and to subsequently remove them after amplification to restore the Oligo nucleotide library to its native form after amplification is described.

Fire et al describe the use of 5' independent ligation of RNA. (Pak and Fire 2007) This method relies on the use of T4Rnl ligase which is a template independent ligase. This ligase requires RNA as the 3' acceptor molecule but can utilize DNA as the 5' phosphate donor molecule. Zhelkovsky describe a ligase that can complete step 3 of ligation while being dysfunctional for step 1 and 2. This enables the ligation of 5' Pre-adenylated oligonucleotides. (Zhelkovsky and McReynolds). As a result this ligase is very efficient at ligation and does not require ATP. ATP can be a competitive inhibitor to ligation as too much ATP can drive the ligation reaction backwards leaving many adenylated oligos as a side product. Zhelkovsky also decribes a novel RNA ligase from *Methanobacterium thermoautotrophicum* (Zhelkovsky and McReynolds). This ligase can ligate single stranded DNA as both an acceptor molecule and a donor molecule in a template independent manner. Kool describes a template independent method for ligation but it requires modified oligonucleotides to perform chemical ligation and not all target oligonucleotides have this desired functional group (Xu and Kool 1997).

With Zhelkovskys' novel ligases one can now imagine ligating primers on the 3' end of a DNA probe library. Li also describe a ligase which can do this given a 10,000 fold excess of donor over acceptor molecules (Li and Weeks 2006). With the proper donor primer design (utilizing a blocked 3' end of the donor primer), double stranding this probe library results in only 1 active 3' hydroxyl on the newly generated second strand. This hydroxyl can become the target for the second primer site to be added. This approach is very analogous to Fire's technique for making 5' independent cloning of RNA except it can now be performed on DNA. The inventive aspect of this method is the combination of this technique with an amplification strategy that removes its PCR primers after amplification and single strands the amplified library to result in a identical but amplified oligonucleotide probe library.

Once Primer sites have been added to both ends of a probe library, PCR can be performed. There are several ways to remove primer sites after PCR but they all have current undesirable properties. Putting Uracils in the primers is one method of digesting the primers after PCR with Uracil specific nucleases. This suffers from being a multi-enzyme digestion as UDG only digests the glycosic bond on one strand. Restriction enzymes are often used to cut the primers off but these suffer from also potentially cutting the internal oligo one is attempting to replicate. Methyl sensitive restriction enzymes can be deployed but they often cut both methylated and non-methylated DNA. Recently a Methyl Dependent class of restriction enzymes have been described (Zheng et al.). Positioning these methyl dependent signals in the PCR primer enables a method which can remove the primer sites after amplification with a single step while avoiding internal digests and multiple enzyme end repair step with the other two methods. See FIGS. 1-4.

Articles such as "a", "an", "the" and the like, may mean one or more than one unless indicated to the contrary or otherwise evident from the context.

The phrase "and/or" as used herein in the specification and in the claims, should be understood to mean "either or both" of the elements so conjoined. Multiple elements listed with "and/or" should be construed in the same fashion, i.e., "one or more" of the elements so conjoined. Other elements may optionally be present other than the elements specifically identified by the "and/or" clause. As used herein in the specification and in the claims, "or" should be understood to have the same meaning as "and/or" as defined above. For example, when used in a list of elements, "or" or "and/or" shall be interpreted as being inclusive, i.e., the inclusion of at least one, but optionally more than one, of list of elements, and, optionally, additional unlisted elements. Only terms clearly indicative to the contrary, such as "only one of" or "exactly one of" will refer to the inclusion of exactly one element of a number or list of elements. Thus claims that include "or" between one or more members of a group are considered satisfied if one, more than one, or all of the group members are present, employed in, or otherwise relevant to a given product or process unless indicated to the contrary. Embodiments are provided in which exactly one member of the group is present, employed in, or otherwise relevant to a given product or process. Embodiments are provided in which more than one, or all of the group members are present, employed in, or otherwise relevant to a given product or process. Any one or more claims may be amended to explicitly exclude any embodiment, aspect, feature, element, or characteristic, or any combination thereof.

Exemplification

Example 1

EPA

Materials and Method for EPA—
Oligos Ordered

```
Oligo 1-
                                                        (SEQ ID NO: 3)
/5PHOS/ATC GAC AAC AAC TCT CCG TCC TCC GTG CG/3SpC3/-
ORDERED Oligo 2-
                                                        (SEQ ID NO: 4)
CGC ACG GAG GA/iMe-dC/GGA GAG TTG TTG TCG AT-
ORDERED Oligo 3-
                                                        (SEQ ID NO: 5)
TTC ACT CCT AGC TT/iMe-dC/TCA TGT AGA GAC TCA C/iBiodT/T
GCC Oligo 4-
                                                        (SEQ ID NO: 6)
/5Phos/GG CAA GTG AGT CTC TAC ATG AGA AGC TAG GAG TGA
A/3SpC3/
```

-continued

ILMN Methyl Primer 1.0
(SEQ ID NO: 7)
AATGATACGGCGACCACCGAGATCTACACTCTTTC/iMe-dC/CTACACGA-ORDERED ILMN Methyl Primer 2.0
(SEQ ID NO: 8)
CAAGCAGAAGACGG/iMe-dC/ATACGAGAT-ORDERED Adenylation of Phosphorylated Oligos.

This can be performed by IDT or Enzymatically with reagents from NEB.
  1 ul (100 um Oligo 1)
  2 ul 1 mM ATP
  2 ul 10× Adenylation buffer
  2 ul Mth Ligase
  13 ul ddH20
  1 hour 65° C.
  5 min 85° C. heat kill.

Methods for Decontamination Procedures.

Figure 5A:
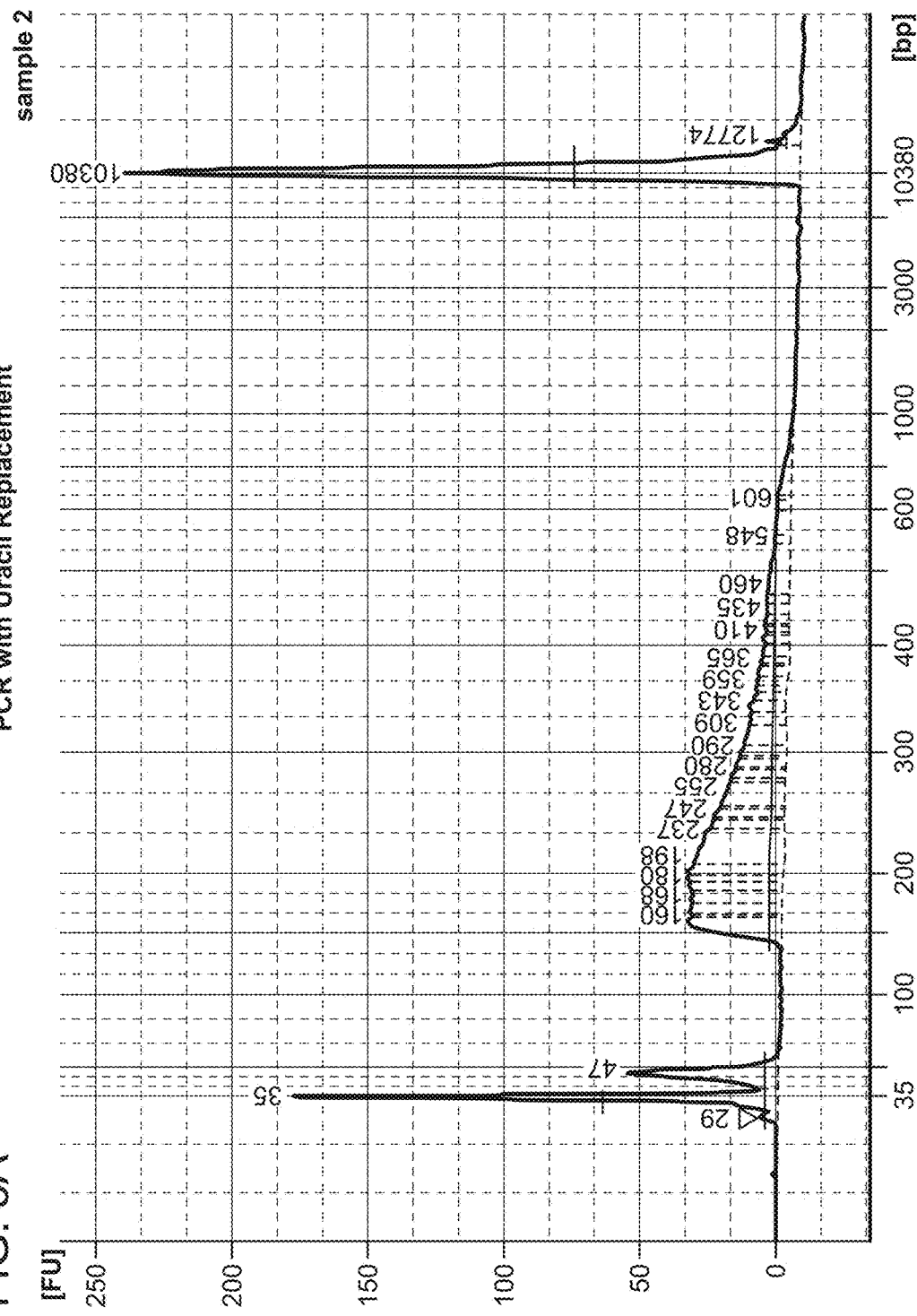
Figure 5B:
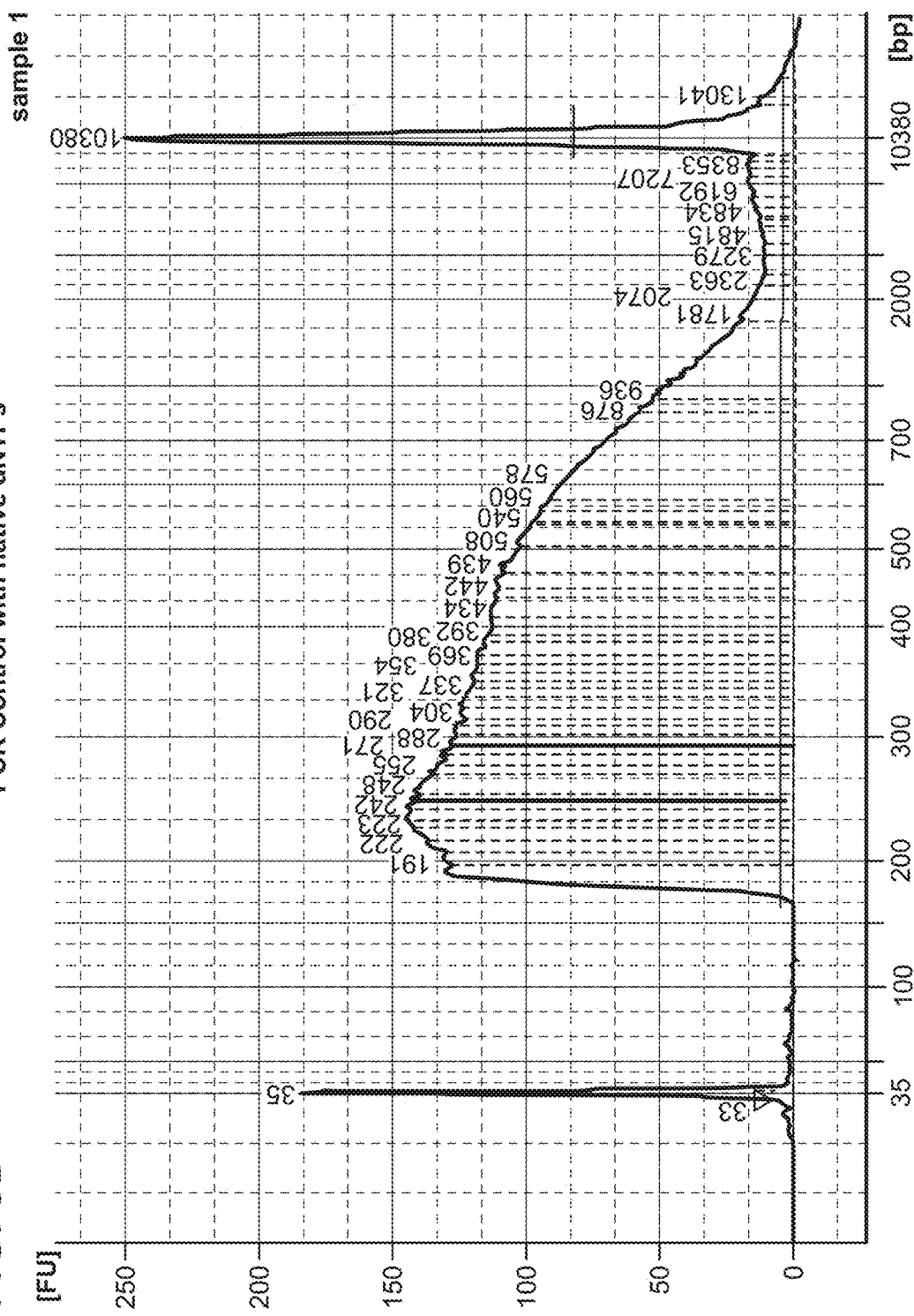

A library for Illumina sequencing was made utilizing the Nextera Kit according to the manufacturers instruction. This library was then PCR amplified with native nucleotides and compared to amplification where dTTP was replaced with dUTP. Kapa Uracil+polymerase was utilized. See FIGS. 5A-5C.
  0.5 ul 10 uM Primer1.0
  0.5 ul 10 uM Primer2.0
  2 ul 2 mM dNTP (dUTP was swapped out at the same concentration as dTTP)
  5 ul 5× Kapa Uracil+buffer
  3 ul DNA (Post Ampured Nextera amplified DNA eluted in 20 ul)
  8 ul ddH20
  1 ul Kapa Uracil+Polymerase (1 U/ul)
  20 ul Total Reaction PCR was performed using the following thermal cycling conditions.
  1) 95° C. for 2 mins
  2) 98° C. for 20 sec
  3) 60° C. for 15 sec
  4) 72° C. for 1 min
  5) Go to 2 for 12 cycles
  6) 72° C. for 3 mins These PCR products were then purified with Ampure according to the manufacturer's recommendations and eluted in 25 ul of ddH20.

1 ul of the eluent was then run on an Agilent Bioanalyzer HS chip to supply the above electropherograms.

Although PCR amplification is more efficient with native nucleotides, complete replacement with Uracil can be amplified with Uracil tolerant polymerases.

5 ul of the Post Ampure Purified Libraries were digested to confirm amplification with dUTP.
  5 ul DNA
  1 ul UDG
  1 ul FpG
  1 ul LifeTech FuPa reagent
  2 ul 10×UDG buffer
  10 ul H20
  37° C. for 30 minutes
  Ampure with 30 ul Ampure Elute in 30 ul ddH20
Load 1 ul on Agilent Bioanalyzer HS chip.

Example 2

Use of 5' Methyl dCTP in PCR and MspJI Digestion for Decontamination

Figure 6:
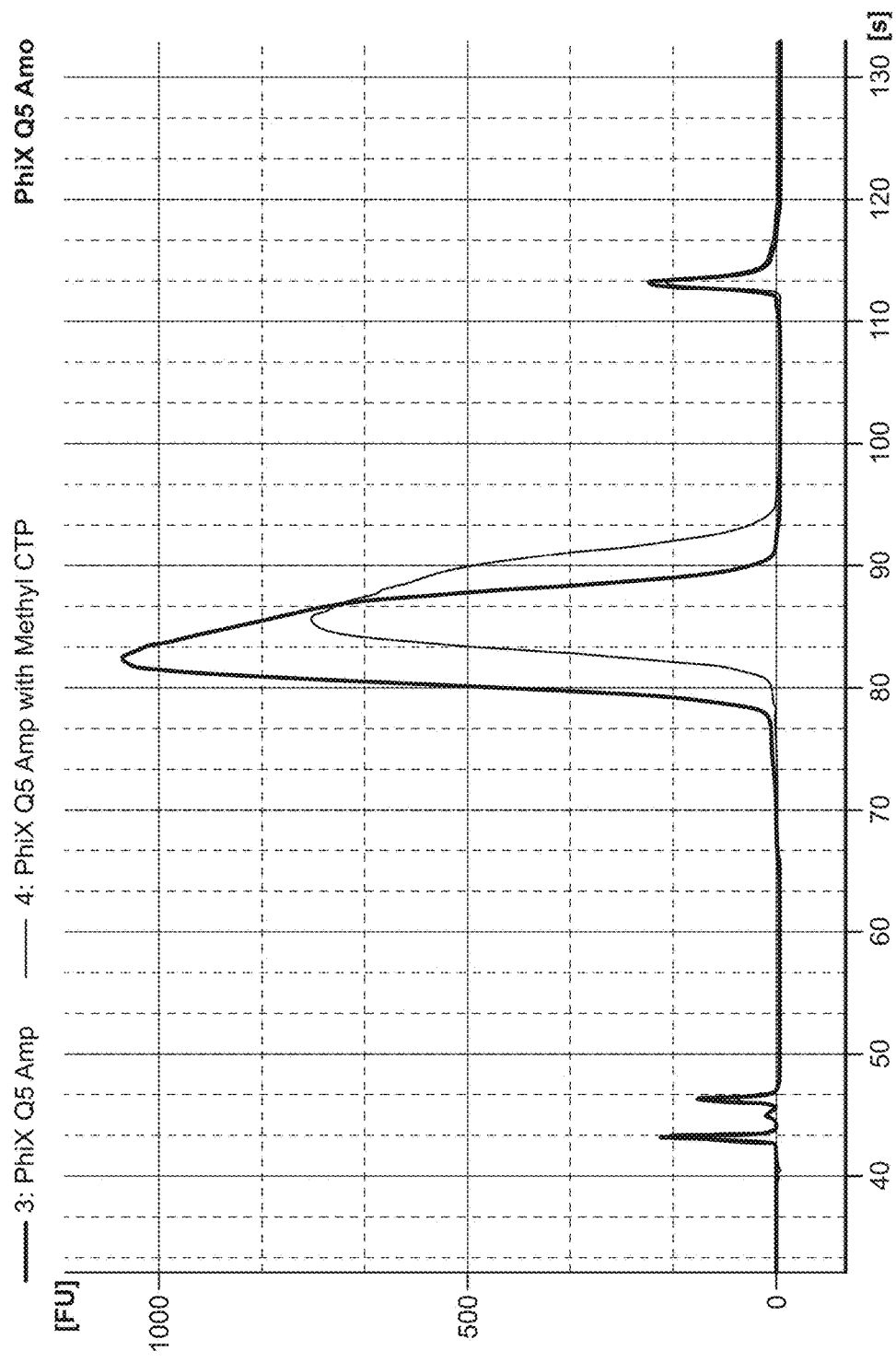
FIG. 6: Methylated amplification

PhiX Library was amplified with and without 5methyl dCTP spiked in.
  17 ul of Q5 Polymerase (NEB)
  2 ul of 10 uM ILMN 1.0 and ILMN 2.0 Primers
  2 ul of 1:100 PhiX control library
  2 ul 5 mM 5methyl dCTP
  11 ul ddH20
  34 ul Reaction
  12 cycles of 12° C.60
  2) 98° C. for 20 sec
  3) 60° C. for 15 sec
  4) 72° C. for 1 min
  5) Go to 2 for 12 cycles
  6) 72° C. for 3 mins 17 ul of the reaction was Ampured with 30 ul. Eluted in 20 ul and 1 ul loaded on an Agilent HS chip. A noticeable gel shift is seen with the methylated amplification. See FIG. 6.

These libraries were both digested with MspJI
  10 ul of Amplification product
  3 ul 10×NEB buffer 4
  1 ul Enzyme Activator
  1 ul 100×BSA
  14 ul ddH20
  1 ul MspJI TipMix and incubate for 37° C. for 1.5 hours.

Ampure 15 ul of reaction with 30 ul of Ampure. Elute in 15 ul. Load 1 ul on Agilent Bioanalyzer.

Figure 7:
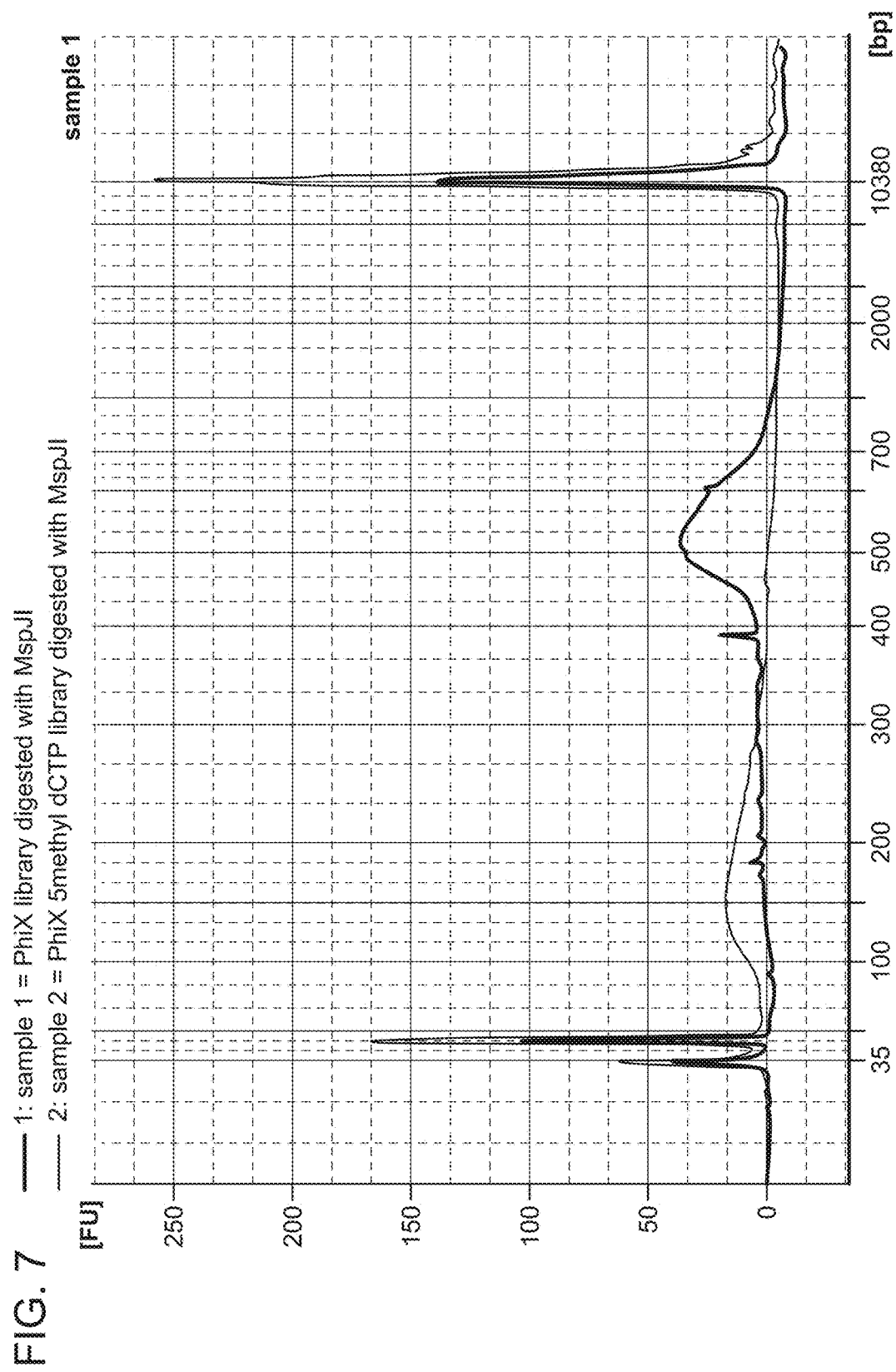
FIG. 7: Digested libraries

The electropherograms in FIG. 7 demonstrate that PCR can be performed with 5' methyl dCTP and that these PCR products can be specifically targeted with methyl specific nucleases like MspJI.

Will methylated libraries amplify and sequence on the Illumina MiSeq sequencer?

Figure 8:
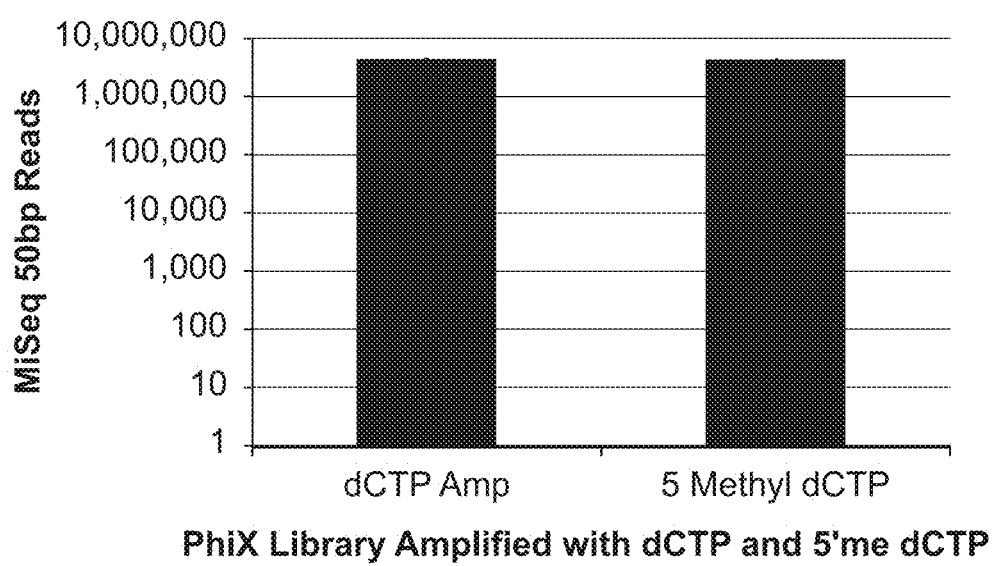
FIG. 8: Graph pf PhiX library amplified with dCTP and 5' me dCTP.

Two PhiX control libraries were amplified as described above. The only modification was the inclusion of a pool of 6 different DNA barcodes for the Control conditions (barcodes 1-6) and 6 different DNA barcodes (7-12) for the 5methyl dCTP amplified library. These libraries were were purified with Ampure and loaded onto the MiSeq according to the manufacturers instructions. 50 bp reads were generated and 6 bases were sequenced for the barcode. Reads were demultiplexed and counted. 4.35 million reads were observed with the control conditions and 4.26M reads were observed with the 5methyl dCTP libraries suggesting the Illumina Miseq can sequence methylated Cytosines in the templates. See FIG. 8.

Can Agilents Haloplex Capture System Utilize 5Methyl dCTP EPA and Produce Sequence?

Figure 9:
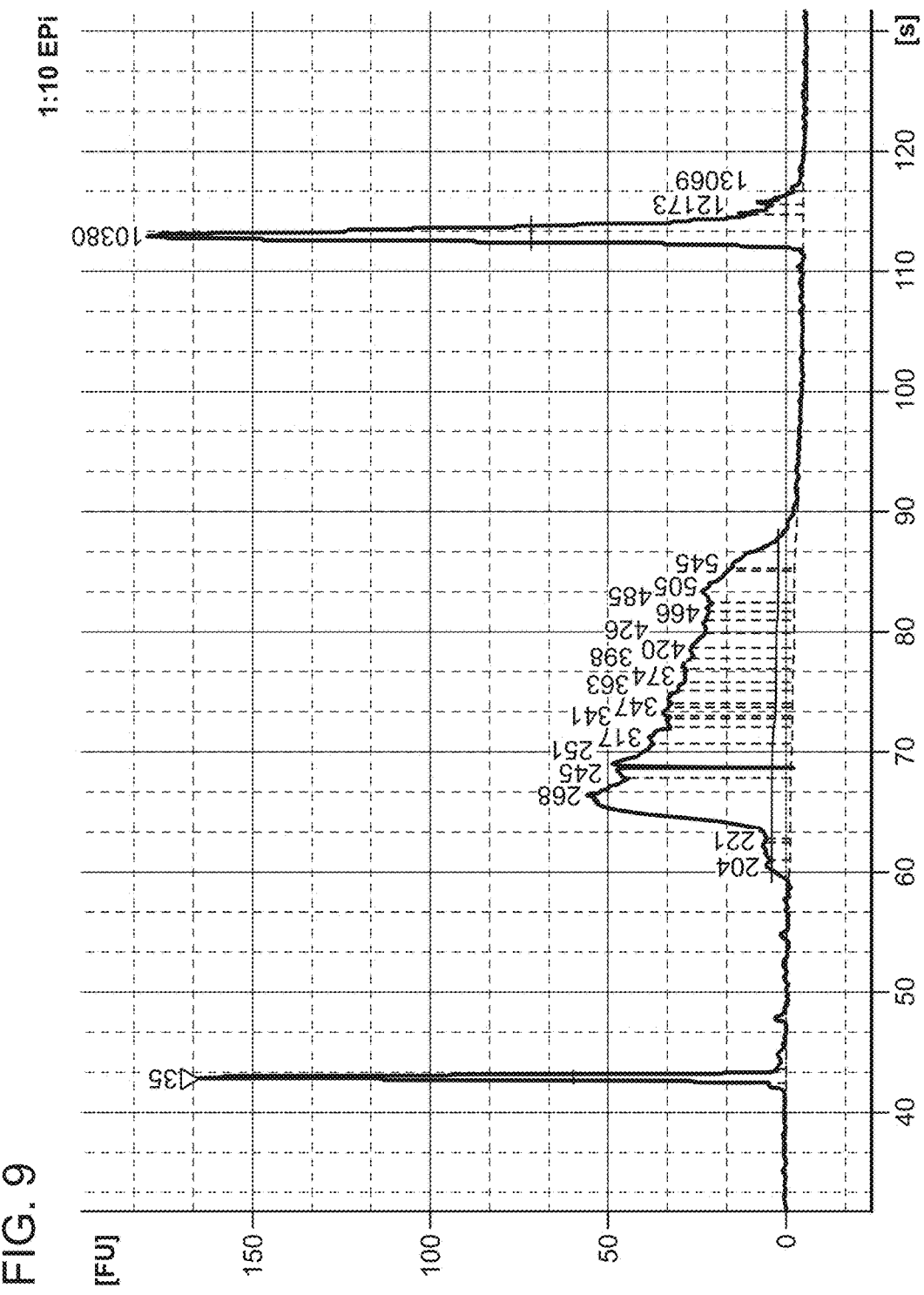
FIG. 9: Electropherogram of amplification with methyl dCTP

Eluted Haloplex NaOH in 40 ul instead of the recommended 25 ul. Took 20 ul and amplified it with the recommended conditions using Herculase PCR. Used remaining 20 ul for 5methyl dCTP PCR with Q5 polymerase.
1) 20 ul DNA
2) 1 ul Primer 1.0 (25 uM)
3) 1 ul Primer 2.0 (25 uM)
4) 0.5 ul 2M Acetic Acid (neutralize NaOH)
5) 2 ul 5 mM 5methyl dCTP
6) 25 ul Q5 2×PCR premix (NEB)
7) Cycle using 18 cycle conditions used for control
98° C. 2:00
98° C. 30 sec
60° C. 30 sec
72° C. 1:00 min
Go to step 2 17 more times
72° C. 4 mins
10° C. forever
Ampure using 1.2× Ampure (60 ul onto 50 ul reaction)
Elute DNA in 40 ul ddH20.
Load 1 ul onto the Agilent HS Bioanalyzer 1 ul of a 1:10 dilution of a 50 ul New England Biolabs Q5 polymerase amplifying with 0.2 mM 5methyl dCTP supplement. Target library was captured with a modified Agilent Haloplex reagent. Library contains 327 genes from Courtagens EpiSEEK panel. This clinical test sequences over 5,000 exons to 200× coverage or more. See FIG. 9.

Figure 10:
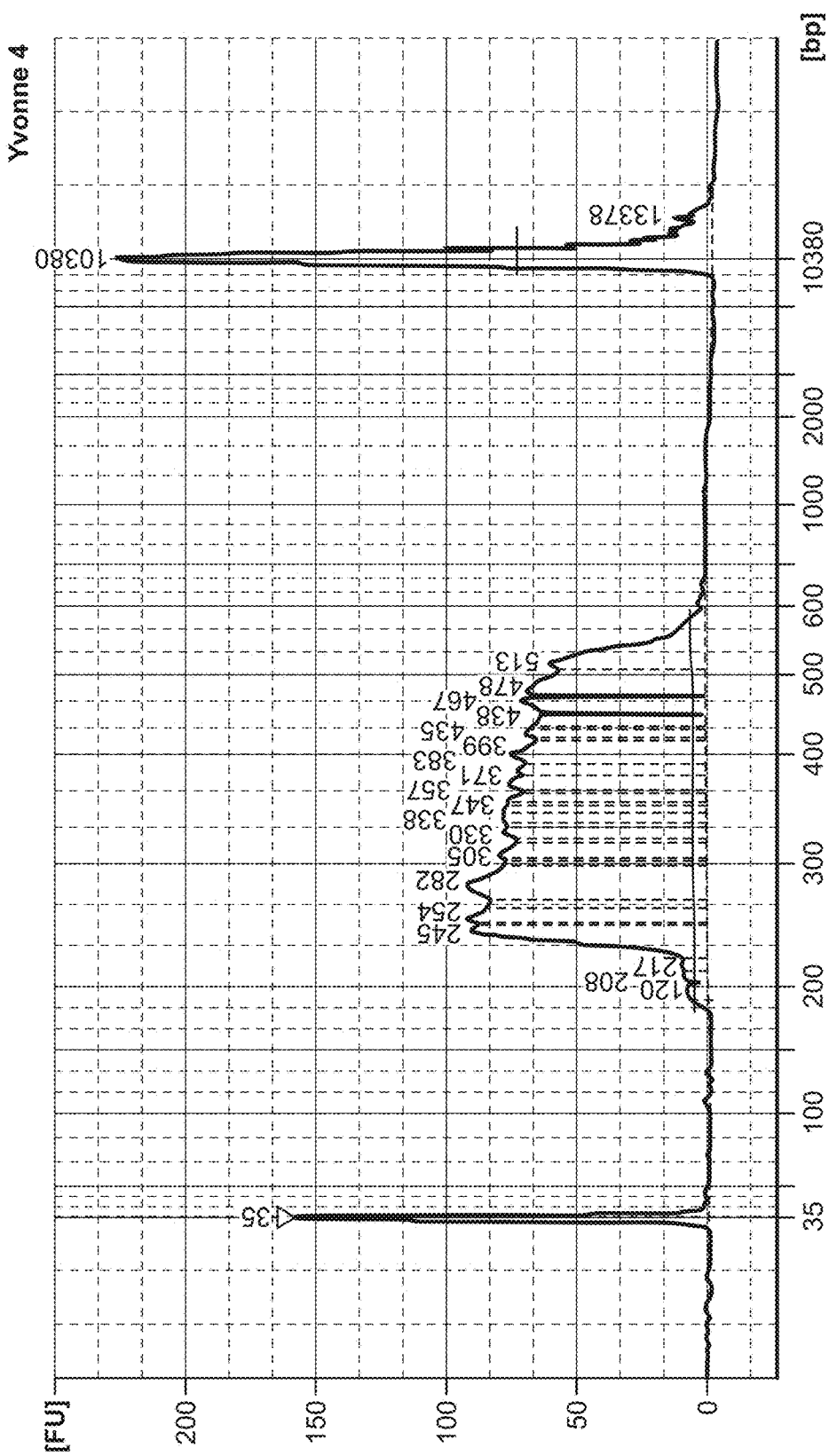
FIG. 10: Electropherogram of amplification with native dCTP

A control library from the same patient was sequenced using the standard protocol utilizing native dCTP. Electropherograms look similar. Methylated library delivered 4.82 ng/ul while the control library delivered 8.0 ng·ul. Libraries were sequenced on the Illumina MiSeq to understand coverage bias. See FIG. 10.

Figure 11:
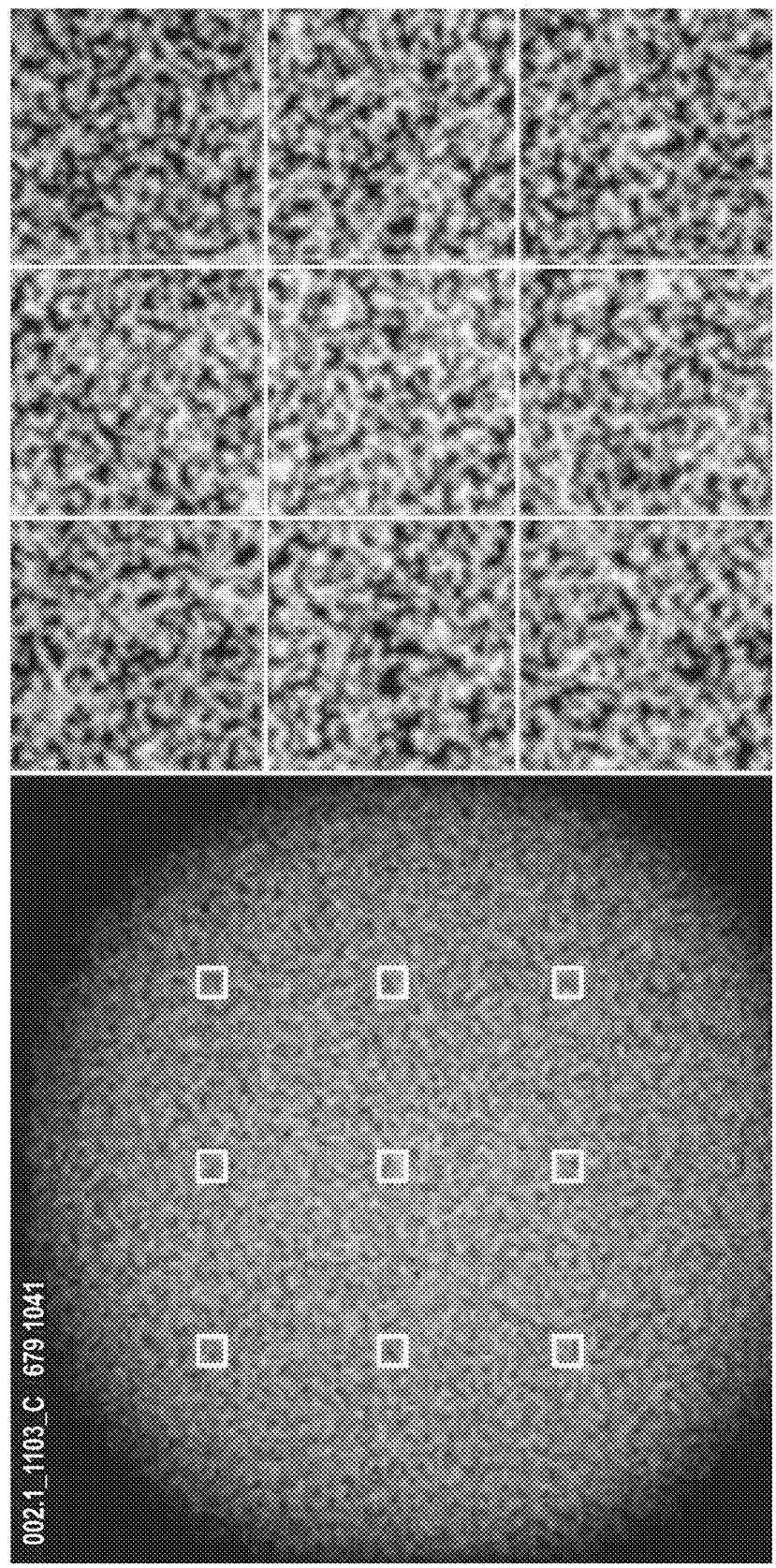
FIG. 11: Clustering results

Libraries were barcoded and loaded on to a MiSeq generating 1.327M clusters per mm^2. No sign of inefficient clustering is seen in the C Channel. 10 Gb run is expected. See FIG. 11.

Figure 12:
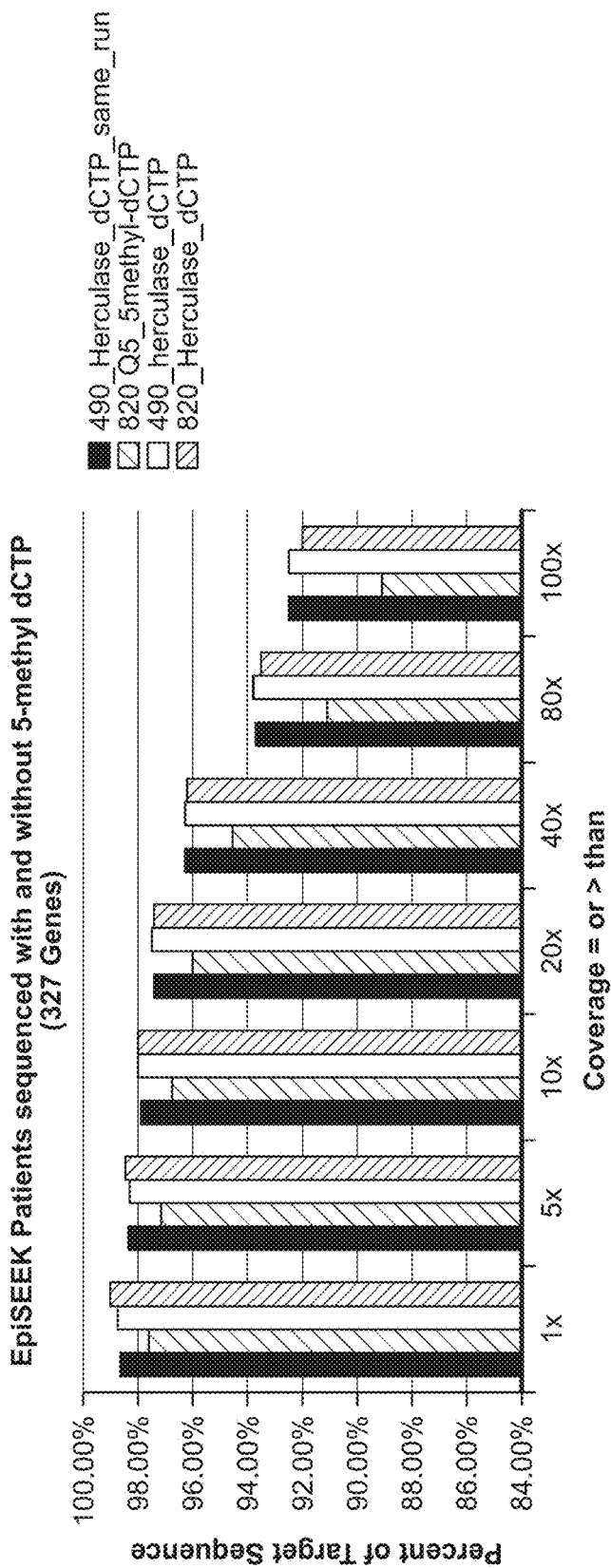
FIG. 12: Results of EpiSEEK patients sequences ith and without 5-methyl dCTP.

5 Million 250 bp reads were generated from 2 patients (490 and 820) using an ILMN MiSeq sequencer with V2 chemistry. Patient 820 was sequenced with both dCTP (purple) and 5-methyl-dCTP(red). Results demonstrate that over 95% of the 5,000 exons targets are sequenced to 20× coverage or higher. Courtagens Clinical cutoff for acceptable data is 90% of the targets covered at least 10× or higher in coverage. See FIG. 12.

Example 3

Déjà Vu PCR: DREAMing and Re-DREAMing PCR Methods

Described herein is a PCR method that utilizes six nucleotides in PCR with two methyl sensitive restriction enzymes that respectively digest these additional nucleotides. Use of this enzyme and nucleotide combination enabled what is termed herein a "DNA diode" where DNA can advance in a laboratory in only one direction and cannot feedback into upstream assays. Aspects of this method that enable consecutive amplification with the introduction of a 5th and 6th base while simultaneously providing mitochondrial DNA enrichment are described.

Methods
Long-Range PCR

PCR setup utilized forward and reverse primers for the 16 kb product: mtPCR6F-321-5'TGGCCACAGCACT-TAAACACATCTC 3' (SEQ ID NO: 9) and mtPCR6R-16191-5'TGCTGTACTTGCTTGTAAGCATGGG3' (SEQ ID NO: 10). PCR was performed utilizing 15 ng of gDNA (10 ng/ul). Reaction setup included 1.5 ul of DNA, 5.0 ul of 10× LA PCR Buffer II, 0.5 ul TaKaRa LA Taq DNA polymerase, 10.65 ul ddH20, and 0.125 ul (50 uM) of each primer with 8.0 ul dNTP mixture (2.5 mM each dNTP where a ratio of 75:25 dCTP:5me-dCTP). The 50 ul PCR reaction was cycled with an initial 1 minute denaturization at 94° C. and is followed by 30 cycles of 98° C. at 10 s, 68° C. for 15 minutes. A final 72° C. 10 minute extension is performed prior to 4° C. hold. PCR products are purified using 75 ul of Ampure (Beckman Genomics).

Nextera Reaction and 5-Hydroxymethylcytosine PCR 3 ul (2.5 ng/ul) of the purified LR-PCR product is used in a 10 ul Nextera reaction (1/20thX) utilizing 5.0 ul TD, 0.25 ul of TDE, 1.75 ul ddH20 (acronyms according to manufacturers instructions). Samples are incubated for 30 minutes at 55° C. followed by a 15 ul Ampure purification. Products are eluted in 25 ul of dH20 and 10 ul of eluent are used for Nextera PCR with 0.75 ul of each 10 uM primer, 1.25 ul of each Illumina index, 20 ul of 2× Q5 polymerase (New England Biolabs) and 0.75 ul of 5 mM 5-hydroxymethyl-cytosine (Trilink) with a 4% final DMSO. 12 Cycles of PCR are performed with the following cycling protocol: 72° C. for 3 minutes, 98° C. for 30 seconds, 12 cycles of 98° C. for 10 seconds, 63° C. for 30 seconds, 72° C. for 1 minute. PCR products are purified using 52.5 ul of Ampure. These products are optionally size selected with a SAGE Sciences Pippin PrepII system in the 600-800 bp size range for 2×250 bp sequencing on a MiSeq V2 sequencer from Illumina according to the manufacturers instructions. Decontamination MspJI digestion is performed with 10 ul DNA (6-8 ng/ul), 1.5 ul 10× buffer, 1.0 ul Activator, 1.5 ul 10×BSA, 0.5 ul MspJI at 37 C for 30 minutes. The sample is heat killed at 65° C. for 20 minutes before initiating PCR.

Figure 16:
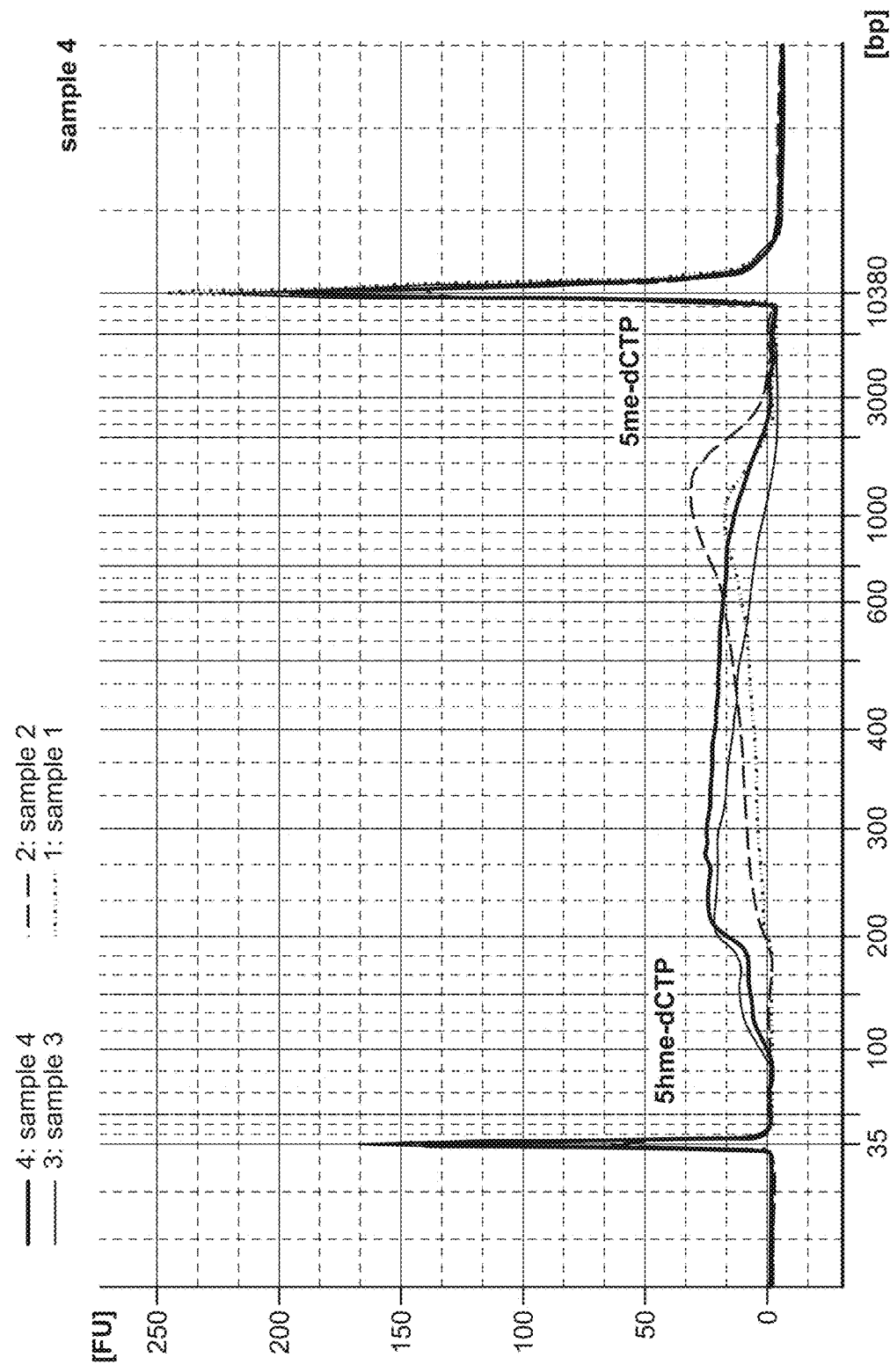
FIG. 16: Following amplification, 10 ul of product (estimated 80 ng) was digested with 5 Units of AbaSI for 1.5 hrs at 25° C. with a 65° C. 20 min heat kill. As suggested by Wang et al, cleavage with AbaSI appears specific to 5hydroxymethylcytosine fragments.

AbaSI digestion is performed with 10 ul DNA (6-8 ng/ul), 1.5 ul 10× buffer, 1.0 ul AbaSI, 2.5 ul ddH20 at 25° C. for 1 hour. The sample is heat killed at 65° C. for 20 minutes before initiating PCR. FIG. 16 demonstrates the decontamination with AbaSI.

Enrichment Ascertainment

Haloplex assays were designed and amplified according to the manufacturers version 2 instructions (Agilent). MspJI digestion was performed as described above but with 1 unit of enzyme. Experiments were DNA barcoded and sequenced with Illumina Miseq V2 sequencer with 2×250 bp reads to ensure high mapping quality. All reads were mapped with Bowtie2 and coverage calculations were performed with BEDTools as previously described (McKernan in press).

Figure 18:
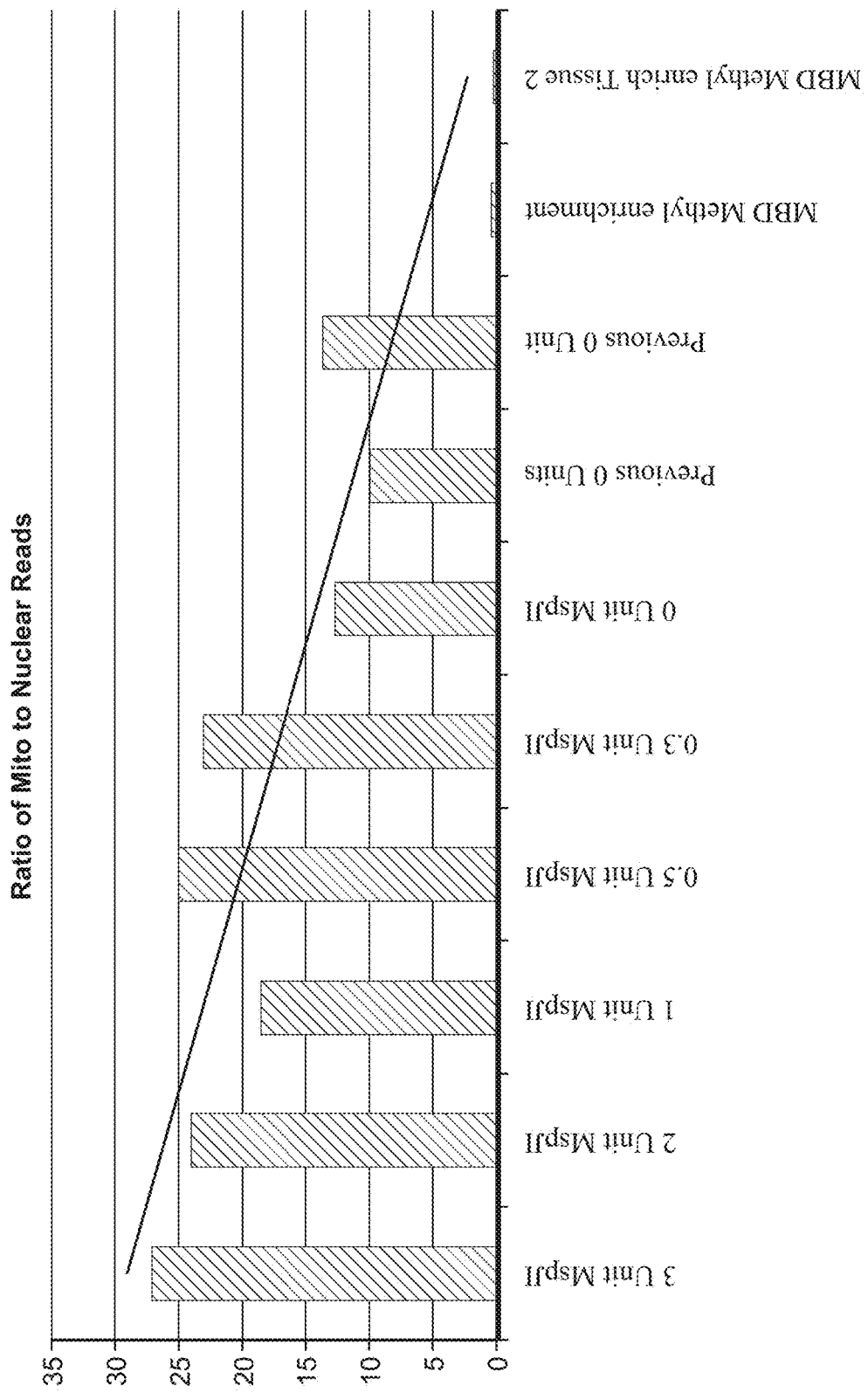
FIG. 18: Ratio of Mitochondrial reads to Nuclear reads using Methyl digestion with MspJI and Methyl enrichment with Methyl Binding Domains.

The control samples demonstrated a M:N ratio of 12.3. Mitochondrial DNA is known to be in several hundred to thousand copies per cell and the M:N amplicon target ratio is 16 kb/246 kb. Since the 246 kb nuclear target is only n=2 in copy number next to an estimated n=500 for Mitochondria, we can adjust the formula to M(n-mito)/N(n-nuc) to get 16 kb*500/246 kb*2 with an expect read ratio of 16. The M:N ratio of the 3 units of MspJI treated gDNA samples is over twice as high (27.3) as the controls (FIG. 18). To further confirm these results we used magnetic particles (New England Biolabs, EpiMark) with Methyl Binding Domain (MBD) to methyl capture and sequence a given sample to demonstrate far lower M:N ratios. The MBD particles deliver confirmatory evidence for differential methylation between Mitochondrial and Nuclear DNA (FIG. 18).

Results

Consecutive amplification utilizes a 6th base.

Several clinically relevant next generation sequencing assays require at least two serial amplification steps. Techniques designed to identify long range genomic phasing often employ whole genome amplification (WGA) before using a more directed PCR approach. In addition, some exome capture techniques require a pre-capture PCR and a post-capture PCR step. Provided herein is a serial PCR which includes an amplification step that comprises a decontaminating methylated cytosine. Specifically, the method is demonstrated herein using 16 kb long range PCR (LR-PCR) to amplify the whole mitochondrial genome for subsequent transposon-mediated library construction, followed by a 12-cycle amplification step (Nextera PCR reaction) using universal Illumina primers.

The serial amplification procedures provided herein utilize universal primers and two different digestible nucleotides, e.g., 5me-dCTP and 5hme-dCTP (Trilink), for exclusive use in respective amplifications. The enzyme AbaSI (NEB) selectively digests 5-hydroxymethylcytosine without digesting 5-methylcytosine.

Figure 13:
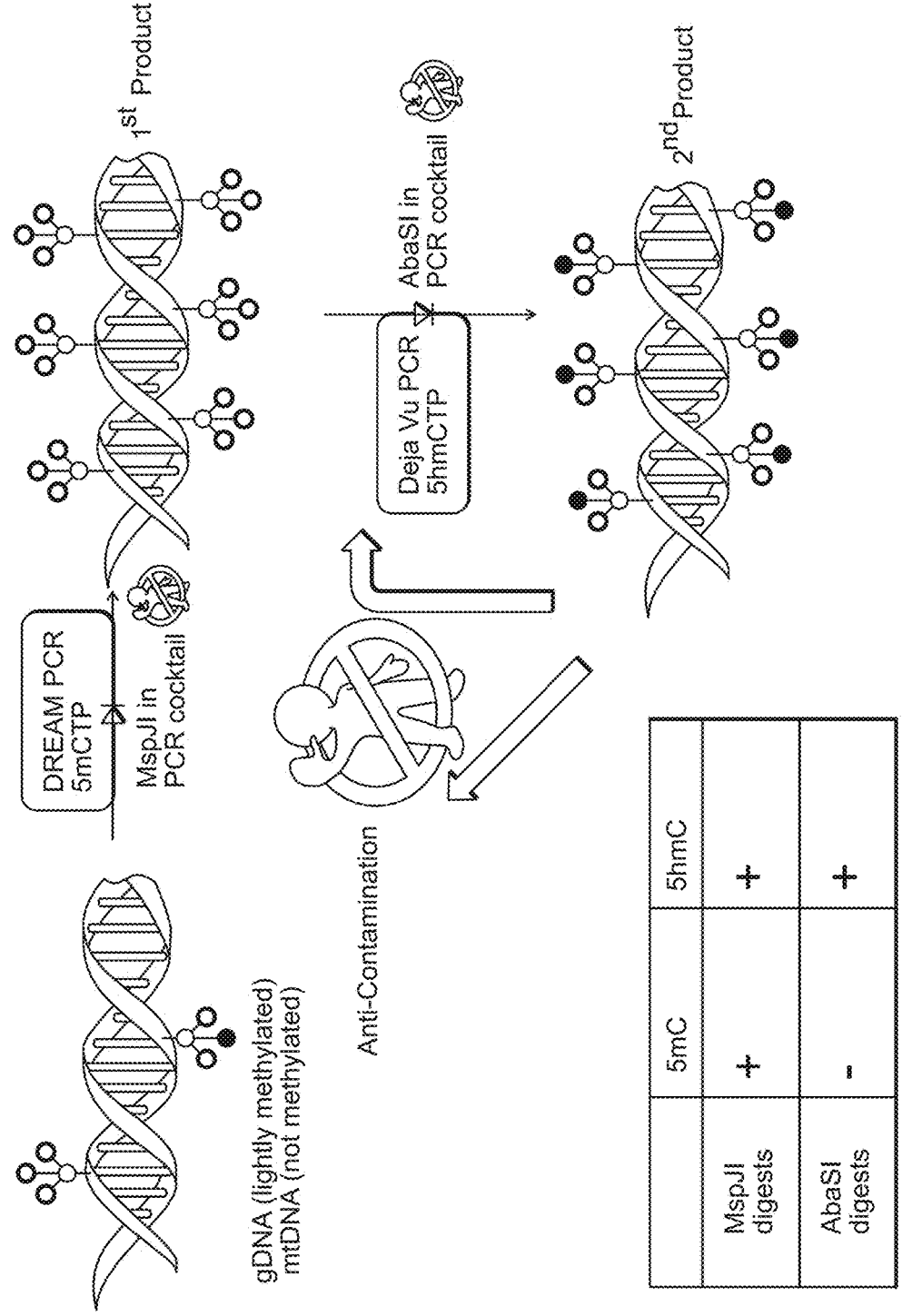
FIG. 13: Déjà vu PCR makes use of what is termed herein a "DNA diode" where enzymes that specifically digest 5th and 6th bases respectively are leveraged to ensure complex serial amplification steps can be performed contamination free without physical isolation of lab equipment. Red dots are Hydroxyl groups, Green dots are Hydrogen, Blue dots are Carbon, thus hydroxymethyl groups have 1 red, 2 green, 1 blue dot while methyl cytosine, have 3 Green dots and 1 Blue dot.

Decontamination techniques work best when the target to be amplified is different than the product or potential contaminant. If 5me-dCTP exists in the first LR-PCR product, one cannot use MspJI to decontaminate the second Nextera PCR reaction, as MspJI is a methyl-specific restriction enzyme and will digest both the substrate 16 kb target amplicon and any potentially contaminating Nextera PCR products. As shown herein, in order for decontamination to be effective the post-amplified (e.g., Nextera) contaminants require a nucleotide (5-hydroxymethylcytosine) that does not exist in the 5-methylcytosine LR-PCR DNA (FIG. 13).

Figure 14:
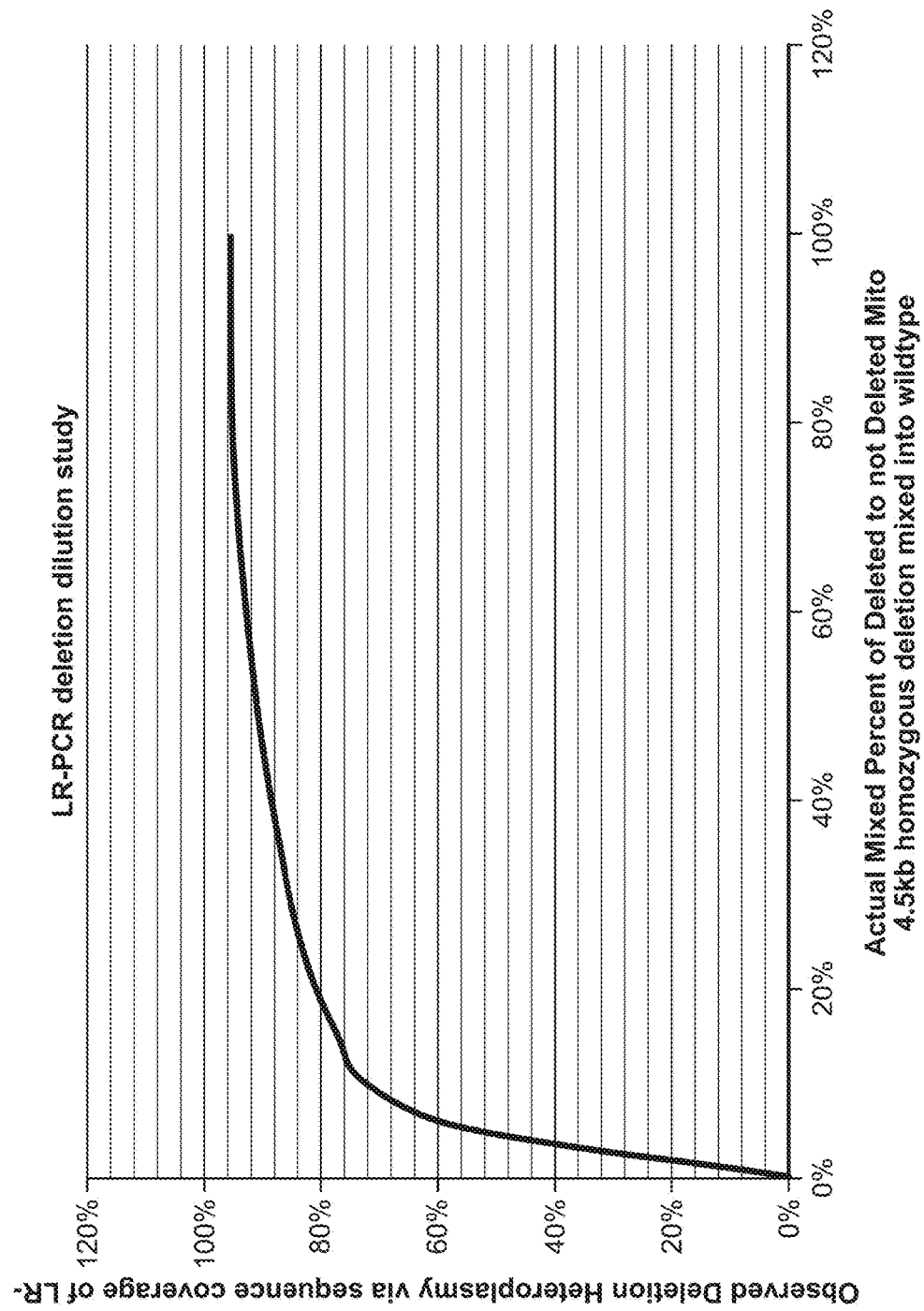
FIG. 14: Observed vs Expected coverage of a mitochondrial DNA deleted sample mixed with a known full length (16.6 kb) wild type mtDNA sample. 4.5 kb Kearns-Sayre homozygous mtDNA deletion was then diluted into a wild-type 16.6 Kb barcoded mitochondrial sample at known mixture ratios, barcoded and sequenced on an ILMN Miseq V2 sequencer. Expected coverage of the known undeleted region vs the observed ratio of these regions was ascertained by barcode demultiplexing and read counting. This result was expected in that a multiplexed 12 Kb PCR proceeds at a more rapid rate than its 16.6 kb PCR competitive product despite 15 minute extension times applied in PCR. This also highlighted the pronounced sensitivity for detecting large deletions in mtDNA samples using LR-PCR.

The described LR-PCR has site-specific primers, thus, contaminants from a Nextera PCR reaction with different universal primers are less likely to create amplifiable contamination. Nevertheless, these Nextera libraries contain mitochondrial DNA, a small portion of which is complementary to the LR-PCR primers and secondary amplification artifacts can in fact amplify and impair heteroplasmy detection. In addition to this source of background, deleted mitochondria from other clinical samples can hyper-amplify if co-present with clinical mtDNA which is significantly longer in length. FIG. 14 demonstrates how a patient with a 4.5 kb mitochondrial deletion known to be associated with Kearns-Sayre syndrome can hyper-amplify (10×) in a foreground of 16.6 Kb target amplification. Thus, the two sources of potential contamination underscore the need for decontamination techniques.

Long Range PCR Considerations

The use of LR-PCR for massively parallel mitochondrial sequencing has proven to have the most sensitive heteroplasmy and large deletion detection. This is largely due to LR-PCR's ability to deliver uniform coverage and to limit the amplification of similar Nuclear MiTochondrial or NUMTs sequences found with methods that use hybridization capture techniques. Nevertheless, LR-PCR methods can be hindered by jumping PCR artifacts with NUMTs and often the heteroplasmy sensitivity is limited to 1% allele frequencies, despite the fact that sequencing techniques can deliver accurate allele frequencies far below this. Since 90% of mtDNA deletions are larger than 2 kb, LR-PCR methods are also prone to hyper-amplification of clinically relevant deleted mtDNA samples. This hyper-amplification is an advantage for clinical sensitivity but also presents a leveraged contamination risk if background deleted mitochondrial samples contaminate other clinical samples.

To address this, described herein is a decontamination approach that concurrently depletes NUMTs from the sample. Prior to initiation of PCR, the sample is digested with MspJI which digests hyper-methylated dsDNA that can otherwise contaminate the LR-PCR. Exhaustive bisulfite sequencing of mitochondria in several tissues has demonstrated complete lack mitochondrial DNA methylation, while NUMTs are rapidly methylated in the nuclear genome. This suggests methyl specific restriction digestion can selectively digest NUMTs and render them non-amplifiable.

During the first LR-PCR amplification a mixture of dCTP and 5-methyl dCTP was used. During the second Nextera PCR a mixture of dCTP and 5-hydroxymethylcytosine was used. Since MspJI digests both 5-methylcytosine and 5-hydroxymethylcytosine, it decontaminated the LR-PCR reaction setup of both past LR-PCR product and past Nextera PCR product contaminants while also digesting NUMTs gDNA. MspJI has a preference of double-stranded DNA over single-stranded DNA and this preference may alter a given application.

Figure 15:
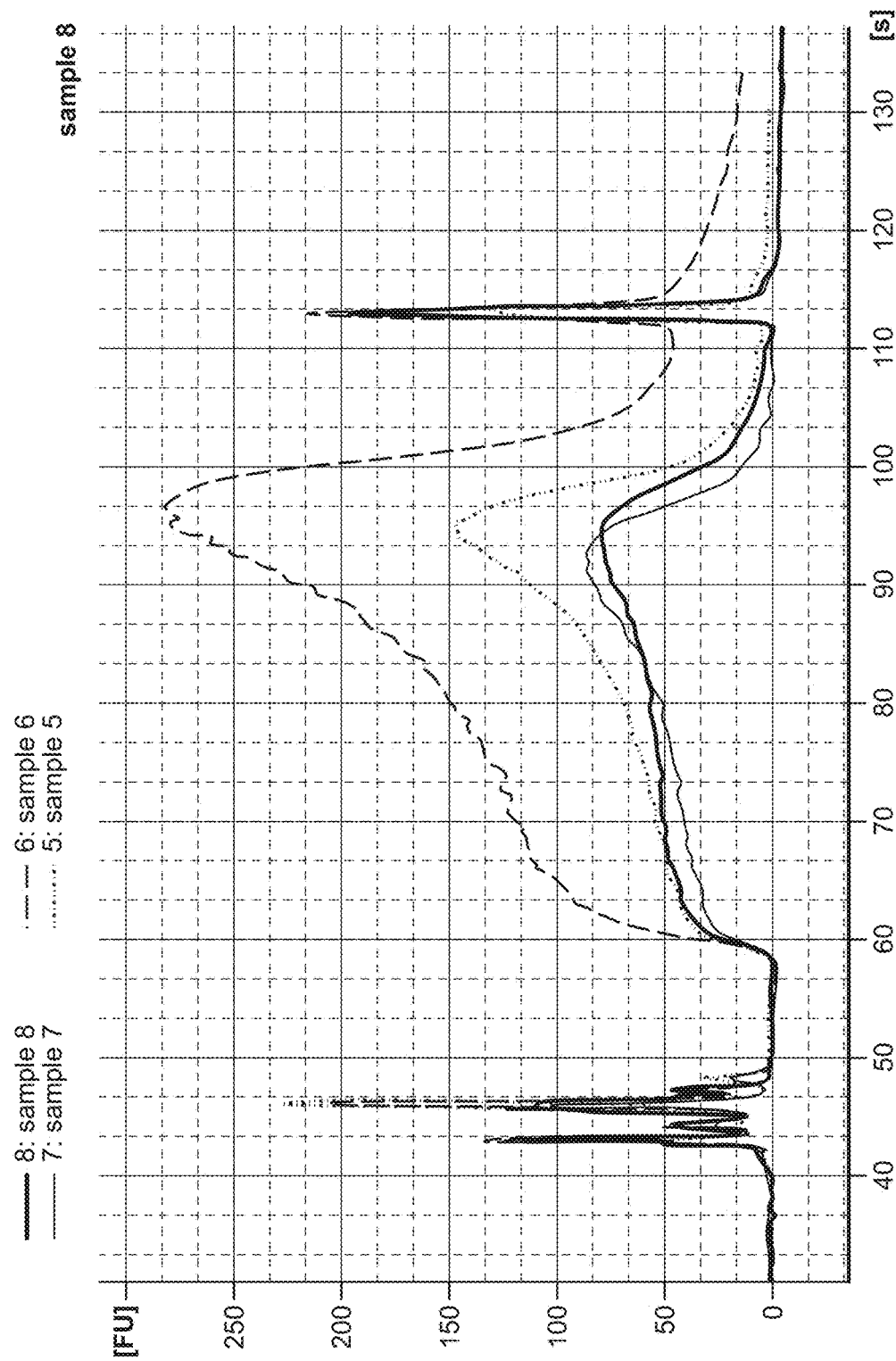

After the first LR-PCR and prior to the second Nextera PCR AbaSI was used to digest contaminants as this enzyme only digests 5-hydroxymethylcytosine, leaving 5-methylcytosine or cytosine intact. In this case, AbaSI only digested PCR products that contaminated the pre-Nextera sample from the post secondary PCR process (FIG. 15). The second PCR usually contains universal sequencing primers producing small products (700 bp) desired by the limitations of current sequencers. These smaller PCR products can hyper-amplify due to cold PCR or other selective amplification biases and as a result can be over represented. Hyper-amplification of contaminants in PCR are the largest risk in a clinical laboratory testing for heteroplasmy.

Decontamination and Optimal Sequencing Performance

Figure 17:
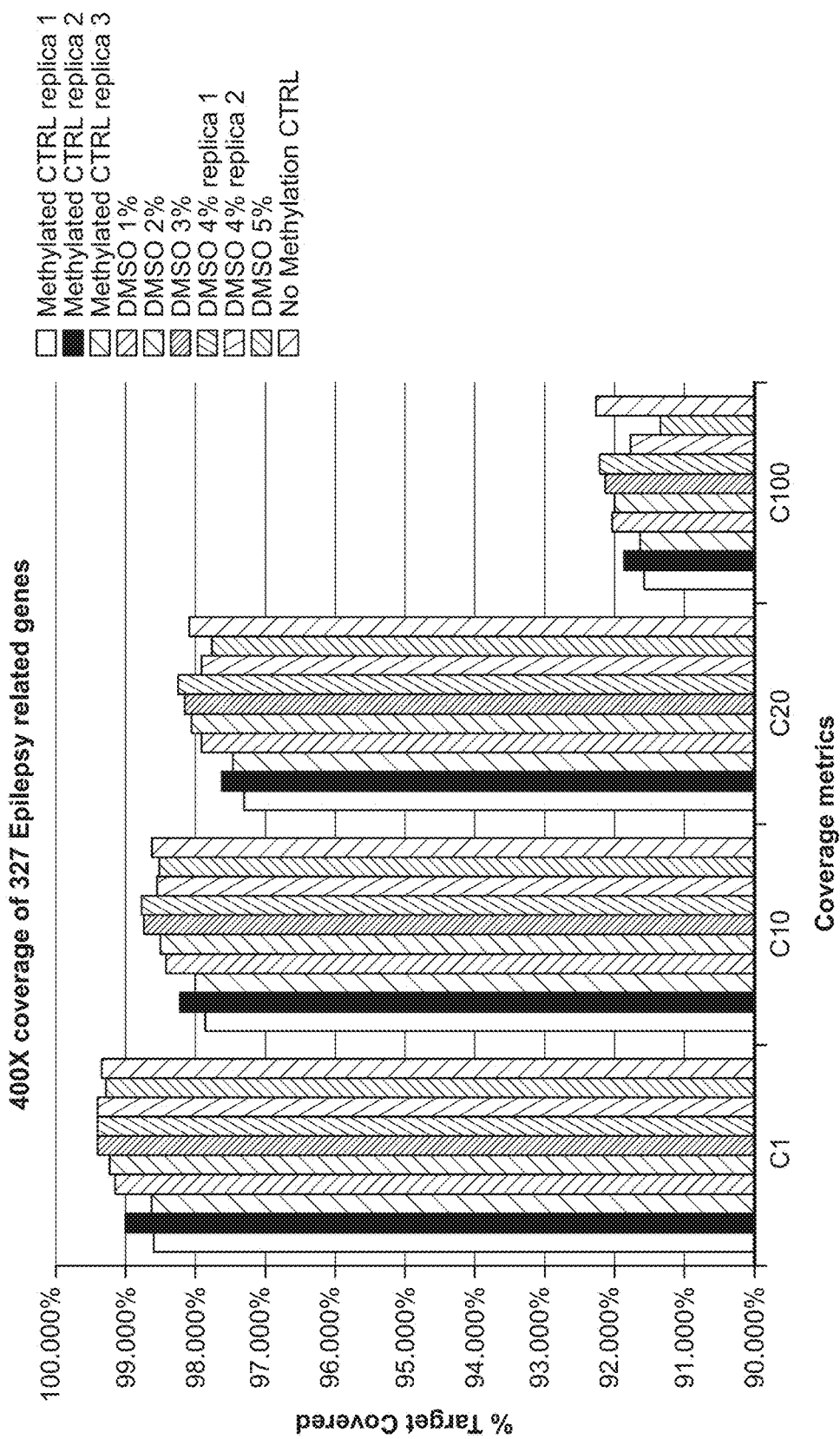
FIG. 17: Use of DMSO is estimated to lower the Tm 0.6° C. per % according to Von Ashen et al. This improves the C20 coverage of targets in sequencing panels.

Since 5-methylcytosine alters the Tm of DNA by 0.5° C. per methylated cytosine, optimizations to the PCR conditions were explored. Previous studies with DREAM PCR demonstrated decaying sequencing coverage with increasing concentrations of 5-methyl dCTP. (McKernan et al) Raising the annealing and denaturization temperatures to compensate for 5-methyl-dCTP's impact on Tm exposes DNA to hydrolytic damage. As a result, methods that alter the solvation and melting temperature without introducing thermal damage to the DNA were pursued. It was found that about a 4% final concentration of DMSO provided optimal sequencing coverage (FIG. 17) equal to non-methylated amplification controls.

Figure 19:
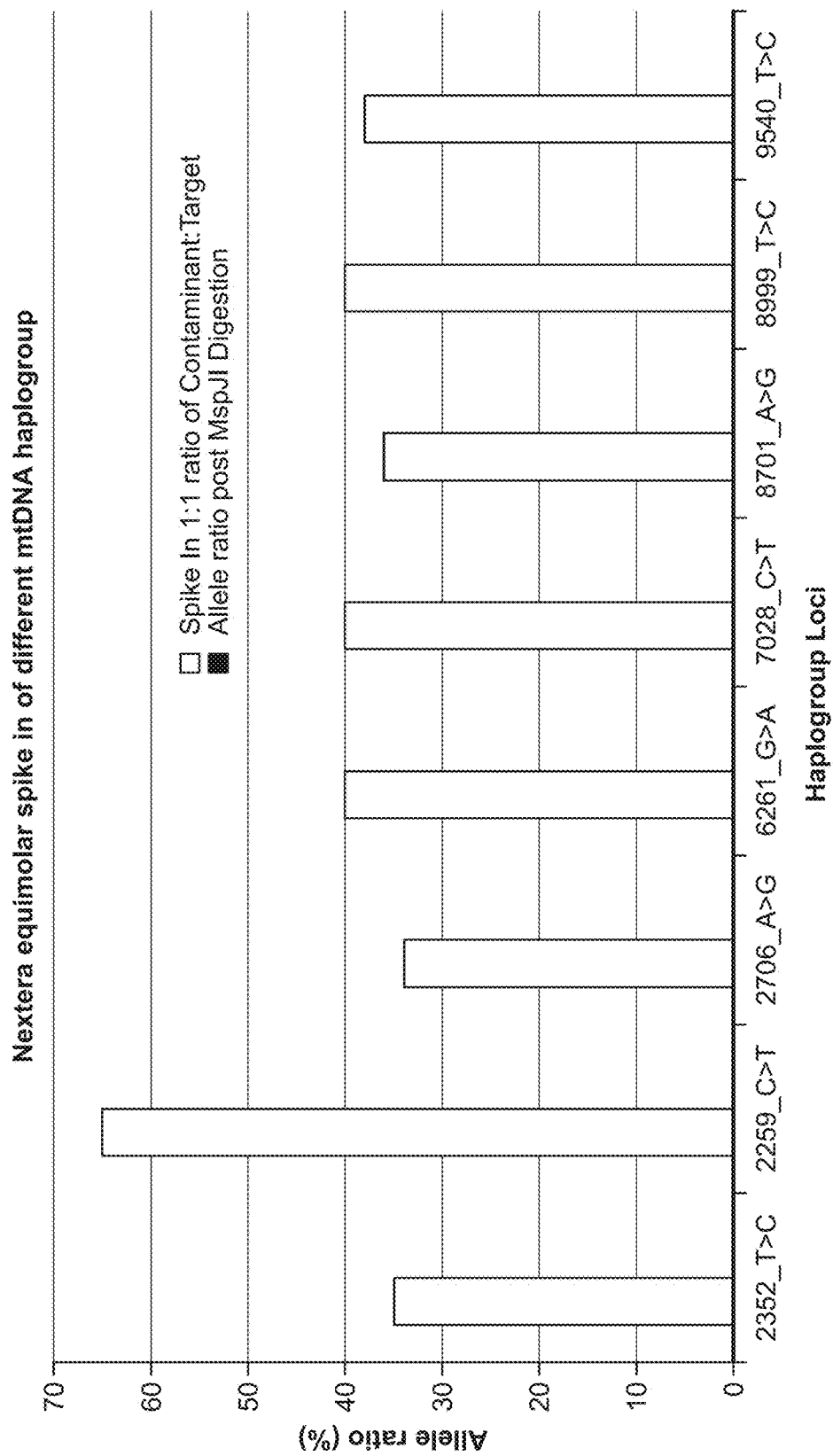
FIG. 19: To measure decontamination potential we spiked in 5me-dCTP amplified mtDNA from a different haplogroup into Target mtDNA to be amplified and measured heteroplasmy levels with and without MspJI decontamination. MspJI digestion removed 100% of expected heteroplasmy contaminants suggesting it can decontaminate equimolar contamination events or less. Note: red bars are at 0% demonstrating complete decontamination at equimolar contamination levels.
Figure 20:
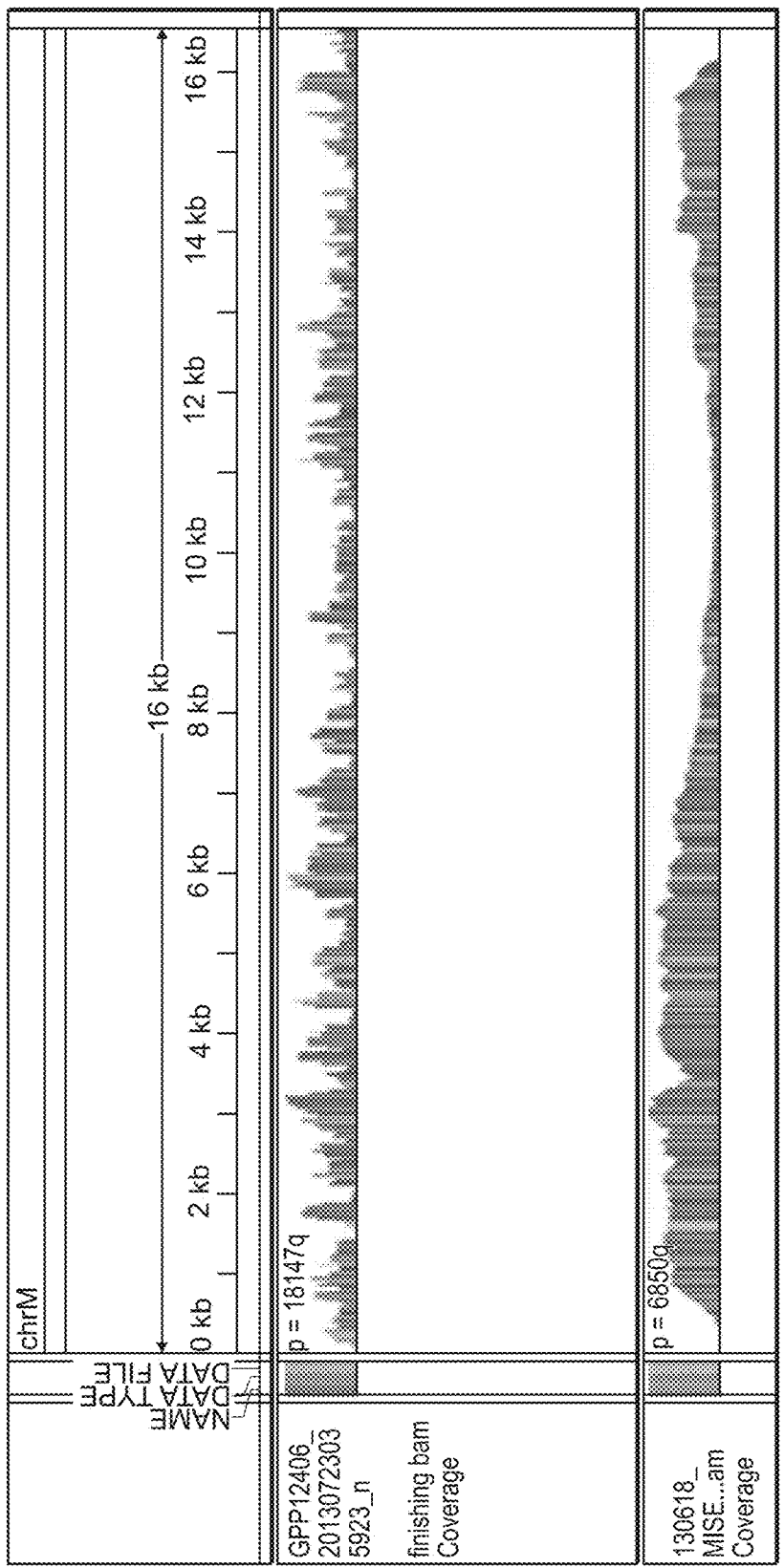
FIG. 20: Haloplex 320 amplicon capture of Mitochondrial DNA provides variable coverage. Long Range PCR makes has more uniform coverage and more obvious deletion detection.
Figure 21:
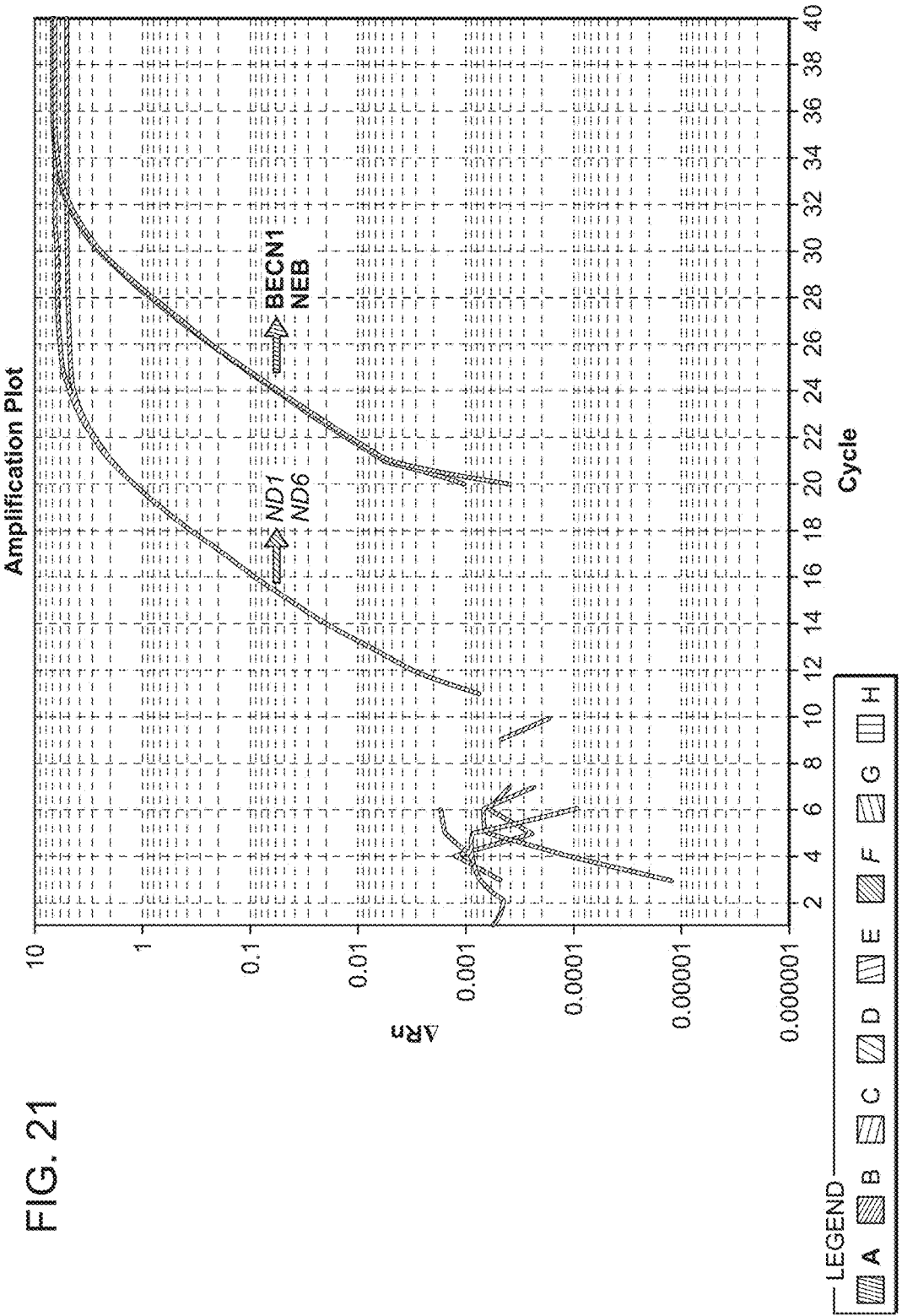
FIG. 21: SYBR Green Real Time PCR estimates mitochondrial copy number at 416 copies next to diploid genes BECN1 and NEB.

Decontamination was measured by spiking in known amounts of DNA contaminant from a different mitochondrial haplogroup. These samples were treated with the respective enzymes and deeply sequenced (10,000×) to measure the percent heteroplasmy of the sample at the haplogroup specific loci. A simple 1 hr digestion was able to remove a 50 fold excess of contaminating DNA (FIG. 19). This assay is limited in that it is only measuring contamination at <40 haplogroup specific loci.

Mitochondrial Enrichment

To measure the mitochondrial DNA enrichment a Haloplex assay that targeted both the entire mitochondrial genome (320 amplicons) and several nuclear genes in parallel (13,060 amplicons) was designed. Genomic DNA was purified and treated with and with out MspJI digestion (0, 0.3, 0.5, 1, 2, 3 units of MspJI enzyme). These libraries were then sequences, and the reads were mapped to hg19 including the mitochondrial genome to measure the ratio of reads mapping to nuclear versus mitochondrial targets. This mapped read ratio was termed the M:N ratio and was used to estimate enrichment. The M:N ratio in the control sample was 12.3 while the MspJI digested sample had a M:N ratio of 27.3, demonstrating an enrichment of mitochondrial DNA through the digestion of methylated gDNA. Quantitative PCR was performed to confirm the M:N ratio of the source DNA (FIG. 18).

DISCUSSION

These results demonstrate additional utility of DREAM PCR in decontaminating more complex amplification procedures than described previously (REF). In addition the importance of such decontamination techniques for mitochondrial sequencing and the impact suppressing large deletion hyper-amplification is underscored. Also demonstrated herein is a beneficial enrichment of mtDNA by leveraging the lack of methylation in mitochondrial DNA. This addresses a problem with NUMTs contaminating many next-generation mitochondrial sequencing assays previously described and likely opens the field for accurate sub percentage heteroplasmy sensitivity.

These results likely have relevance for accurate sequencing in any sample that demands low allele frequency quantification like heterogeneous biopsies. Likewise, the results underscore the value in generating ephemeral PCR products. With recent concerns over DNA confidentiality and the ease of de-identification of DNA samples, data encryption is becoming a standard in clinical laboratory data management to prevent in-silico contamination or disclosure of DNA sequence. Considering physical DNA can be harvested from 50,000 year old samples, a clinical laboratory's trash is a confidentiality exposure point if DNA is not digested or destroyed during testing. Thus methods that eliminate DNA from a clinical laboratory offer attractive and responsible features. In summary, a method that improves DREAM PCR sequencing performance while providing more freedom to operate concurrently with a more responsible clinical management of patient DNA is provided herein.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method of removing amplicons of a non target nucleic acid having one or more cytosines that are methylated from a sample wherein the sample comprises amplicons of the non target nucleic acid and genomic DNA that includes a target nucleic acid to be serially amplified, the target nucleic acid having one or more methylated cytosines, comprising
   a) contacting the sample with a composition comprising (i) deoxynucleotide triphophates (dNTPs) comprising dATP, dTTP, dGTP, and dCTP wherein one or more of the dCTP nucleotides are methylated with a first methyl group (ii) a nucleic acid polymerase, (iii) one or more primers that are complementary to a portion of the target nucleic acid, and (iv) a first methyl specific restriction enzyme that is capable of being deactivated and that digests nucleic acids comprising nucleotides that are methylated with the first methyl group, thereby producing a combination;
   b) maintaining the combination under conditions in which the amplicons of the non target nucleic acid are digested by the first methyl specific restriction enzyme prior to amplification of the genomic DNA that includes the target nucleic acid;
   c) amplifying the genomic DNA that includes the target nucleic acid, thereby producing amplicons of the target nucleic acid having one or more nucleotides that are methylated with the first methyl group;
   d) contacting the amplicons of the target nucleic acid with a composition comprising (i) deoxynucleotide triphophates (dNTPs) comprising dATP, dTTP, dGTP, and dCTP wherein one or more of the dCTP nucleotides are methylated with a second methyl group (ii) a nucleic acid polymerase, (iii) one or more primers that are complementary to a portion of the target nucleic acid, and (iv) a second methyl specific restriction enzyme that is capable of being deactivated and that selectively digests nucleic acids comprising nucleotides that are methylated with the second methyl group, thereby producing a combination;
   e) maintaining the combination of e) under conditions in which the amplicons of the non target nucleic acid are digested by the second methyl specific restriction enzyme prior to amplification of the genomic DNA that includes the target nucleic acid; and
   f) amplifying the genomic DNA that includes the target nucleic acid, thereby producing amplicons of the target nucleic acid having one or more nucleotides that are methylated with the first methyl group and the second methyl group, wherein the amplicons of the non target nucleic acid are removed from the sample comprising the genomic DNA that includes the target nucleic acid to be serially amplified.

2. The method of claim 1, wherein the methyl specific restriction enzyme is deactivated upon a change in temperature, a change in pH, contact with a reagent or a combination thereof.

3. The method of claim 1, wherein the dCTP nucleotides that are methylated with a first methyl group are 5-methyl cytosine nucleotides, and the dCTP nucleotides that are methylated with a second methyl group are 5-hydroxymethyl cytosine nucleotides.

4. The method of claim 1, wherein the first methyl specific restriction enzyme is selected from the group consisting of MspJ1, FspE1, LpnPI, AspBHI, RlaI, SgrTI, and AbaSI.

5. The method of claim 1, wherein the second methyl specific restriction enzyme is selected from the group consisting of MspJ1, FspE1, LpnPI, AspBHI, RlaI, SgrTI, and AbaSI.

6. The method of claim 3, wherein the first methyl specific restriction enzyme is MspJI.

7. The method of claim 3, wherein the second methyl specific restriction enzyme is AbaSI.

8. The method of claim 6, wherein the second methyl specific restriction enzyme is AbaSI.

9. The method of claim 1, wherein the composition of a) further comprises one or more reagents that alters the melting temperature.

10. The method of claim 9, wherein the one or more reagents comprises dimethyl sulfoxide (DMSO), Tri-methyl glycine (Betaine) or a combination thereof.

11. The method of claim 1, wherein the non target nucleic acid is double stranded.

12. The method of claim 1, wherein the non-target nucleic acid is a nucleic acid library, genomic nucleic acid, or mitochondrial nucleic acid, or a combination thereof.

13. The method of claim 1, wherein the genomic DNA that includes the target nucleic acid is denatured prior to amplification.

14. The method of claim 1, wherein the target nucleic acid is amplified for at least 1 amplification cycle, wherein each amplification cycle comprises 12° C. for 60 seconds, 98° C. for 20 seconds, 60° C. for 15 seconds, 72° C. for 60 seconds, 12 sequencing cycles at 98° C. for 20 seconds, 72° C. for 3 minutes.

* * * * *

SEQUENCE LISTING

```
<160> NUMBER OF SEQ ID NOS: 10

<210> SEQ ID NO 1
<211> LENGTH: 53
<212> TYPE: DNA
<213> ORGANISM: Unknown
<220> FEATURE:
<223> OTHER INFORMATION: methylated DNA sequence

<400> SEQUENCE: 1
tggtaataat aaggttgagg acttttttccg gatgcccgga atgggttcaa agg          53

<210> SEQ ID NO 2
<211> LENGTH: 53
<212> TYPE: DNA
<213> ORGANISM: Unknown
<220> FEATURE:
<223> OTHER INFORMATION: methylated DNA sequence

<400> SEQUENCE: 2
cctttgaacc cattccgggc atccggaaaa agtcctcaac cttattatta cca          53

<210> SEQ ID NO 3
<211> LENGTH: 29
<212> TYPE: DNA
<213> ORGANISM: Unknown
<220> FEATURE:
<223> OTHER INFORMATION: oligo 1

<400> SEQUENCE: 3
atcgacaaca actctccgtc ctccgtgcg                                      29

<210> SEQ ID NO 4
<211> LENGTH: 29
<212> TYPE: DNA
<213> ORGANISM: Unknown
<220> FEATURE:
<223> OTHER INFORMATION: oligo 2
<220> FEATURE:
<221> NAME/KEY: misc_feature
<222> LOCATION: (12)...(12)
<223> OTHER INFORMATION: m5C

<400> SEQUENCE: 4
```
cgcacggagg acggagagtt gttgtcgat                                    29

<210> SEQ ID NO 5
<211> LENGTH: 36
<212> TYPE: DNA
<213> ORGANISM: Unknown
<220> FEATURE:
<223> OTHER INFORMATION: oligo 3
<220> FEATURE:
<221> NAME/KEY: misc_feature
<222> LOCATION: (15)...(15)
<223> OTHER INFORMATION: m5C
<220> FEATURE:
<221> NAME/KEY: misc_feature
<222> LOCATION: (32)...(32)
<223> OTHER INFORMATION: biotin

<400> SEQUENCE: 5
ttcactccta gcttctcatg tagagactca cttgcc                            36

<210> SEQ ID NO 6
<211> LENGTH: 36
<212> TYPE: DNA
<213> ORGANISM: Unknown
<220> FEATURE:
<223> OTHER INFORMATION: oligo 4

<400> SEQUENCE: 6
ggcaagtgag tctctacatg agaagctagg agtgaa                            36

<210> SEQ ID NO 7
<211> LENGTH: 44
<212> TYPE: DNA
<213> ORGANISM: Unknown
<220> FEATURE:
<223> OTHER INFORMATION: ILMN Methyl Primer 1.0
<220> FEATURE:
<221> NAME/KEY: misc_feature
<222> LOCATION: (36)...(36)
<223> OTHER INFORMATION: m5C

<400> SEQUENCE: 7
aatgatacgg cgaccaccga gatctacact ctttccctac acga                   44

<210> SEQ ID NO 8
<211> LENGTH: 24
<212> TYPE: DNA
<213> ORGANISM: Unknown
<220> FEATURE:
<223> OTHER INFORMATION: ILMN Methyl Primer 2.0
<220> FEATURE:
<221> NAME/KEY: misc_feature
<222> LOCATION: (15)...(15)
<223> OTHER INFORMATION: m5C

<400> SEQUENCE: 8
caagcagaag acggcatacg agat                                         24

<210> SEQ ID NO 9
<211> LENGTH: 25
<212> TYPE: DNA
<213> ORGANISM: Unknown
<220> FEATURE:
<223> OTHER INFORMATION: forward primer for mtPCR6F-321

<400> SEQUENCE: 9
tggccacagc acttaaacac atctc                                        25

```
<210> SEQ ID NO 10
<211> LENGTH: 25
<212> TYPE: DNA
<213> ORGANISM: Unknown
<220> FEATURE:
<223> OTHER INFORMATION: reverse primer mtPCR6R-16191

<400> SEQUENCE: 10
tgctgtactt gcttgtaagc atggg                                              25
```